(12) United States Patent
Kelly et al.

(10) Patent No.: US 9,932,392 B2
(45) Date of Patent: Apr. 3, 2018

(54) PREVENTION OF INFECTION

(71) Applicants: CSL Behring AG, Bern (CH); BETH ISRAEL DEACONESS MEDICAL CENTER INC, Boston, MA (US)

(72) Inventors: Ciaran Kelly, West Newton, MA (US); Xinhua Chen, Malden, MA (US); Sylvia Miescher, Bern (CH); Martin Spycher, Lyss (CH); Sandra Wymann, Bern (CH); Adrian Zuercher, Bern (CH)

(73) Assignees: CSL BEHRING AG, Bern (CH); BETH ISRAEL DEACONESS MEDICAL CENTER INC, Boston, MA (US)

( * ) Notice: Subject to any disclaimer, the term of this patent is extended or adjusted under 35 U.S.C. 154(b) by 0 days.

(21) Appl. No.: 14/383,962

(22) PCT Filed: Mar. 8, 2013

(86) PCT No.: PCT/EP2013/054701
§ 371 (c)(1),
(2) Date: Sep. 9, 2014

(87) PCT Pub. No.: WO2013/132054
PCT Pub. Date: Sep. 12, 2013

(65) Prior Publication Data
US 2015/0017181 A1 Jan. 15, 2015

(30) Foreign Application Priority Data

Mar. 9, 2012 (EP) .................................... 12158933

(51) Int. Cl.
| | | |
|---|---|---|
| C07K 16/12 | (2006.01) |
| A61K 39/40 | (2006.01) |
| A61K 38/14 | (2006.01) |
| A61K 39/395 | (2006.01) |
| A61K 45/06 | (2006.01) |
| A61K 38/17 | (2006.01) |
| A61K 39/00 | (2006.01) |

(52) U.S. Cl.
CPC .......... *C07K 16/1282* (2013.01); *A61K 38/14* (2013.01); *A61K 38/1774* (2013.01); *A61K 39/395* (2013.01); *A61K 39/40* (2013.01); *A61K 45/06* (2013.01); *A61K 2039/505* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 5,258,177 A | 11/1993 | Uemura et al. | |
| 5,410,025 A | 4/1995 | Moller et al. | |
| 5,500,345 A | 3/1996 | Soe et al. | |
| 6,069,236 A | 5/2000 | Burnouf-Radosevich et al. | |
| 6,300,104 B1 | 10/2001 | Morrison et al. | |
| 6,307,028 B1 | 10/2001 | Lebing et al. | |
| 6,646,108 B1 | 11/2003 | Leibl et al. | |
| 6,696,620 B2 * | 2/2004 | Hiatt ..................... | C07K 16/00 435/219 |
| 6,967,106 B2 | 11/2005 | Simon | |
| 7,597,891 B2 * | 10/2009 | Simon ................. | A61K 31/415 424/130.1 |
| 7,749,721 B2 * | 7/2010 | Alonso-Garcia ...... | C07K 14/47 435/7.9 |
| 7,794,721 B2 | 9/2010 | Simon | |
| 8,021,645 B2 * | 9/2011 | Simon ................ | C07K 16/1282 424/130.1 |
| 8,119,104 B2 * | 2/2012 | Simon .................. | C07K 16/065 424/130.1 |
| 8,313,730 B2 * | 11/2012 | Simon .................. | C07K 16/065 424/130.1 |
| 8,709,413 B2 * | 4/2014 | Simon .................... | C07K 16/00 424/130.1 |
| 9,505,847 B2 * | 11/2016 | Cassan ............... | C07K 16/1282 |
| 9,522,184 B2 | 12/2016 | Von Gunten et al. | |
| 9,546,209 B2 * | 1/2017 | Aebi ...................... | C07K 16/06 |
| 2003/0082643 A1 | 5/2003 | Hudson et al. | |
| 2004/0132979 A1 | 7/2004 | Chtourou et al. | |
| 2004/0199945 A1 * | 10/2004 | Hiatt ...................... | C07K 16/00 800/288 |
| 2008/0145371 A1 * | 6/2008 | Simon .................. | A61K 31/415 424/176.1 |
| 2008/0145420 A1 * | 6/2008 | Simon ................... | A61K 38/14 424/463 |

(Continued)

FOREIGN PATENT DOCUMENTS

| | | |
|---|---|---|
| CN | 1500097 A | 5/2004 |
| EP | 0 413 188 A2 | 2/1991 |

(Continued)

OTHER PUBLICATIONS

Prinsloo et al, Protein Expression and Purification, 2006, 47:179-185.*
Per Brandtzaeg, Int. J. Med. Microbiol. 293, 3 ± 15 (2003).*
Olson et al, J Trauma Acute Care Surg, 2013, vol. 74, No. 4, pp. 983-990.*
Johnson, International J. of Antimicrobial Agents, 2009, 33, S1:S33-S36.*
Brandtzaeg, Int. J. Med. Microbiol., 2003, 293:3-15.*
Johansen et al, Scand. J. Immunol., 2000, 52:240-248.*

(Continued)

*Primary Examiner* — Nita M. Minnifield
(74) *Attorney, Agent, or Firm* — Birch, Stewart, Kolasch & Birch, LLP

(57) ABSTRACT

The invention relates to compositions and methods to prevent enteric infection in a subject at risk of such infection. In particular, the invention relates to the prevention of recurrence of infection by *Clostridium difficile*.

21 Claims, 8 Drawing Sheets

(56) References Cited

U.S. PATENT DOCUMENTS

| | | | |
|---|---|---|---|
| 2010/0322872 | A1 | 12/2010 | Perraudin |
| 2013/0210164 | A1 | 8/2013 | Gagnon |
| 2013/0338344 | A1 | 12/2013 | Ramasubramanyan et al. |
| 2014/0348935 | A1* | 11/2014 | Simon .................. C07K 16/16 424/499 |
| 2014/0371431 | A1* | 12/2014 | Brown ................ C07K 16/065 530/390.5 |
| 2015/0005476 | A1* | 1/2015 | El Menyawi .......... C07K 16/00 530/389.1 |
| 2015/0017181 | A1* | 1/2015 | Kelly ..................... A61K 38/14 424/150.1 |
| 2015/0030613 | A1* | 1/2015 | Aebi ...................... C07K 16/06 424/164.1 |
| 2015/0056180 | A1* | 2/2015 | Corthesy ............. C07K 16/065 424/130.1 |
| 2017/0051047 | A1* | 2/2017 | Berry ................. C07K 16/1282 |
| 2017/0058018 | A2* | 3/2017 | Brown ................ C07K 16/065 |

FOREIGN PATENT DOCUMENTS

| | | |
|---|---|---|
| EP | 0 703 922 A1 | 4/1996 |
| EP | 0 839 915 A1 | 5/1998 |
| JP | 2000-103800 A | 4/2000 |
| WO | WO 94/29334 A1 | 12/1994 |
| WO | WO 95/04081 A1 | 2/1995 |
| WO | WO 97/25352 A1 | 7/1997 |
| WO | WO 98/57993 A1 | 12/1998 |
| WO | WO 99/64462 A1 | 12/1999 |
| WO | WO 00/41721 A1 | 7/2000 |
| WO | WO 2001/083806 * | 11/2001 |
| WO | WO 02/076502 A1 | 10/2002 |
| WO | WO 02/092632 A1 | 11/2002 |
| WO | WO 03/015817 A2 | 2/2003 |
| WO | WO 2004/012763 A1 | 2/2004 |
| WO | WO 2005/047337 A1 | 5/2005 |
| WO | WO 2009/46168 A1 | 4/2009 |
| WO | WO 20091139624 A1 | 11/2009 |
| WO | WO 2011/131786 A2 | 10/2011 |

OTHER PUBLICATIONS

Longet et al, The Journal of Biological Chemistry vol. 289, No. 31, pp. 21617-21626, Aug. 1, 2014.*
Mantis et al, Mucosal Immunology, Nov. 2011, 4/6:603-611.*
Phalipon et al, Trends in Immunology, Feb. 2003, 24/2:55-58.*
Westerhof et al, Frontiers in Plant Science, Jan. 11, 2016, 6:Article 1200, 12 pages.*
Wijburg et al, J. Experimental Medicine, published Jan. 3, 2006, 203/1:21-26.*
Phalipon et al, Immunity, Jul. 2002, 17:107-115.*
Longet et al, Journal Biological Chemistry, Feb. 8, 2013, 288/6:4085-4094.*
Longet et al, Human Plasma-derived Polymeric IgA and IgM Antibodies Associate with Secretory Component to Yield Biologically Active Secretory-like antibodies. JBC, Feb. 8, 2013, 288/6:4085-4094 (Year: 2013).*
Brandtzaeg, Complex Formation Between Secretory Component and Human Immunoglobulins Related to Their Content of J Chain. Scand. J. Immunol., 1976, 5:411-419 (Year: 1976).*
Brandtzaeg. Characteristics of Sc-Ig Complexes formed in vitro. IN: The Immunoglobulin a System, eds. J. Mestecky et al. 1974, pp. 87-97. (Year: 1974).*
Australian Patent Examination Report No. 1, dated Oct. 25, 2013, for Australian Application No. 2013201389.
Bartlett et al., "Antibiotic-Associated Pseudomembranous Colitis Due to Toxin-Producing Clostridia", The New England Journal of Medicine, vol. 298, No. 10, Mar. 9, 1978, pp. 531-534.
Bauer et al., "Alternative strategies for Clostridium difficile infection", International Journal of Antimicrobial Agents, vol. 33, No. S1, 2009, pp. S51-S56.
Chen et al., "A Mouse Model of Clostridium difficile-Associated Disease", Gastroenterology, vol. 135, No. 6, Dec. 2008, pp. 1984-1992.

Coia, "What is the role of antimicrobial resistance in the new epidemic of Clostridium difficile?", International Journal of Antimicrobial Agents, vol. 33, No. S1, 2009, pp. S9-S12.
Dallas et al., "Binding of Clostridium difficile toxin A to human milk secretory component", J. Med. Microbiol., vol. 47, 1998, pp. 879-888.
Denève et al., "New trends in Clostridium difficile virulence and pathogenesis", International Journal of Antimicrobial Agents, vol. 33, No. S1, 2009, pp. S24-S28.
Extended European Search Report, dated Aug. 29, 2012, for European Application No. 12158933.7.
Gastmeier et al., "Surveillance of Clostridium difficile-associated diarrhoea with the German nosocomial infection surveillance system KISS (CDAD-KISS)", International Journal of Antimicrobial Agents, vol. 33, No. S1, 2009, pp. S19-S23.
Gerding, "Clostridium difficile 30 years on: what has, or has not, changed and why?", International Journal of Antimicrobial Agents, vol. 33, No. S1, 2009, pp. S2-S8.
Gorkiewicz, "Nosocomial and antibiotic-associated diarrhoea caused by organisms other than Clostridium difficile", International Journal of Antimicrobial Agents, vol. 33, No. S1, 2009, pp. S37-S41.
Hu et al., "Prospective Derivation and Validation of a Clinical Prediction Rule for Recurrent Clostridium difficile Infection", Gastroenterology, vol. 136, No. 4, Apr. 2009, pp. 1206-1214.
International Preliminary Report on Patentability and Written Opinion of the International Searching Authority (Forms PCT/IB/326, PCT/IB/373 and PCT/ISA/237), dated Sep. 18, 2014, for International Application No. PCT/EP2013/054701.
International Search Report and Written Opinion of the International Searching Authority (Forms PCT/ISA/220, PCT/ISA/237 and PCT/ISA/210), dated Jun. 17, 2013, for International Application No. PCT/EP2013/054701.
Johnson, "Recurrent Clostridium difficile infection: causality and therapeutic approaches", International Journal of Antimicrobial Agents, vol. 33, No. S1, 2009, pp. S33-S36.
Joost et al., "Characterisation of Clostridium difficile isolates by slpA and tcdC gene sequencing", International Journal of Antimicrobial Agents, vol. 33, No. S1, 2009, pp. S13-S18.
Kelly et al., "Clostridium difficile—More Difficult Than Ever", The New England Journal of Medicine, vol. 359, No. 18, Oct. 30, 2008, pp. 1932-1940.
Kuijper et al., "Emergence of Clostridium difficile-associated disease in North America and Europe", Clinical Microbiology and Infection, vol. 12, Supplement 6, 2006, pp. 2-18.
Lowy et al., "Treatment with Monoclonal Antibodies against Clostridium difficile Toxins", The New England Journal of Medicine, vol. 362, No. 3, Jan. 21, 2010, pp. 197-205.
Merrigan et al., "New approach to the management of Clostridium difficile infection: colonisation with non-toxigenic C. difficile during daily ampicillin or ceftriaxone administration", International Journal of Antimicrobial Agents, vol. 33, No. S1, 2009, pp. S46-S50.
Miller et al., "Comparison of the Burdens of Hospital-Onset, Healthcare Facility-Associated Clostridium difficile Infection and of Healthcare-Associated Infection due to Methicillin-Resistant . . . ", Infection Control and Hospital Epidemiology, vol. 32, No. 4, Apr. 2011, pp. 387-390.
Phalipon et al., "Novel functions of the polymeric Ig receptor: well beyond transport of immunoglobulins", Trends in Immunology, vol. 24, No. 2, Feb. 2003, pp. 55-58.
Phalipon et al., "Secretory Component: A New Role in Secretory IgA-Mediated Immune Exclusion In Vivo", Immunity, vol. 17, Jul. 2002, pp. 107-115, XP009107491.
Pituch, "Clostridium difficile is no longer just a nosocomial infection or an infection of adults", International Journal of Antimicrobial Agents, vol. 33, No. S1, 2009, pp. S42-S45.
Rodloff et al., "Introduction", International Journal of Antimicrobial Agents, vol. 33, Supplement 1, 2009, pp. S1-S56 (p. S1 only provided).
Surawicz et al., "Treatment of refractory and recurrent Clostridium difficile infection", Nature Reviews, vol. 8, Jun. 2011 (published online Apr. 19, 2011), pp. 330-339.

(56) References Cited

OTHER PUBLICATIONS

Weiss, "Clostridium difficile and fluoroquinolones: is there a link?", International Journal of Antimicrobial Agents, vol. 33, No. S1, 2009, pp. S29-S32.
Lullau, E., et al, "Antigen Binding Properties of Purified Immunoglobulin A and Reconstituted Secretory Immunoglobulin A Antibodies," The Journal of Biological Chemistry, Jul. 5, 1996, vol. 271, No. 27, pp. 16300-16309.
U.S. Appl. No. 15/384,140, filed Dec. 19, 2016.
U.S. Appl. No. 14/377,535, filed Aug. 8, 2014.
U.S. Appl. No. 14/380,521, filed Aug. 22, 2014.
Aebi et al., "A Protective Epitope of Moraxella catarrhalis is Encoded by Two Different Genes," Infection and Immunity, vol. 65, No. 11, Nov. 1997, pp. 4367-4377 (Total 12 pages).
Aebi et al., "Phenotypic Effect of Isogenic uspA1 and uspA2 Mutations on Moraxella catarrhalis 035E," Infection and Immunity, vol. 66, No. 7, Jul. 1998, pp. 3113-3119 (Total 8 pages).
Australian Office Communication dated Nov. 25, 2013, for Australian Application No. 2013201393.
Australian Patent Examination Report for Australian Application No. 2013201394, dated Dec. 4, 2013.
Australian Patent Examination Report No. 1 dated Nov. 22, 2013, in Australian Application No. 2013201388.
Berdoz et al., "In vitro comparison of the antigen-binding and stability properties of the various molecular forms of IgA antibodies assembled and produced in CHO cells," Proceedings of the National Academy of Sciences, vol. 96, No. 6, Mar. 16, 1999, pp. 3029-3034.
Blijlevens et al., "Palifermin (recombinant keratinocyte growth factor-1): a pleiotropic growth factor with multiple biological activities in preventing chemotherapy- and radiotherapy-induced mucositis," Annals of Oncology, vol. 18, No. 5, May 2007 (Published online Oct. 9, 2006), pp. 817-826.
Bonner et al., "Solution Structure of Human Secretory Component and Implications for Biological Function," The Journal of Biological Chemistry, vol. 282, No. 23, Jun. 8, 2007, pp. 16969-16980.
Bonner et al., "Solution structure of recombinant human secretory component and its two- and three-domain fragments by scattering, ultracentrifugation and constrained modeling," Molecular Immunology, vol. 44, Jan. 1, 2007, p. 156, abstract only.
Bootsma et al., "Analysis of Moraxella catarrhalis by DNA Typing: Evidence for a Distinct Subpopulation Associated with Virulence Traits," The Journal of Infectious Diseases, vol. 181, 2000 (Electronically published Apr. 13, 2000), pp. 1376-1387.
Brach et al., "Ionizing Radiation Induces Expression of Interleukin 6 by Human Fibroblasts Involving Activation of Nuclear Factor-κB," The Journal of Biological Chemistry, vol. 268, No. 12, Apr. 25, 1993, pp. 8466-8472.
Brooks et al., "Moraxella catarrhalis Binding to Host Cellular Receptors Is Mediated by Sequence-Specific Determinants Not Conserved among All UspA1 Protein Variants," Infection and Immunity, vol. 76, No. 11, Nov. 2008 (Aug. 4, 2008), pp. 5322-5329 (Total 9 pages).
Chinese Office Action and Search Report with English translations thereof, dated May 6, 2014, for Chinese Application No. 201180060034.4.
Cohn et al., "Preparation and Properties of Serum and Plasma Proteins. IV. A System for the Separation into Fractions of the Protein and Lipoprotein Components of Biological Tissues and Fluids," J. Am. Chem. Soc., vol. 68, Mar. 1946, pp. 459-475.
Cope et al., "Characterization of the Moraxella catarrhalis uspA1 and uspA2 Genes and Their Encoded Products," Journal of Bacteriology, vol. 181, No. 13, Jul. 1999, pp. 4026-4034 (Total 10 pages).
Corthésy et al., "A Pathogen-specific Epitope Inserted into Recombinant Secretory Immunoglobulin A is Immunogenic by the Oral Route," The Journal of Biological Chemistry, vol. 271, No. 52, Dec. 27, 1996, pp. 33670-33677.
Corthésy et al., "In vitro assembly of secretory immunoglobulin A (sIgA) from IgA and recombinant secretory component," Journal of Cellular Biochemistry, Jan. 5, 1995, p. 244, abstract only.
Corthesy et al., "Molecular Definition of the Role of Secretory Component in Secretory IgA-Mediated Protection at Mucosal Surfaces," Journal of Allergy and Clinical Immunology, vol. 109, No. 1, Jan. 1, 2002, p. S113, abstract only.
Corthésy et al., "Secretory Immunoglobulin A: from Mucosal Protection to Vaccine Development," Biological Chemistry, vol. 380, Nov. 1999, pp. 1251-1262.
Corthésy, "Recombinant immunoglobulin A: powerful tools for fundamental and applied research," Trends in Biotechnology, vol. 20, No. 2, Feb. 2002, pp. 65-71.
Corthésy, "Recombinant Secretory Immunoglobulin A in Passive Immunotherapy: Linking Immunology and Biotechnology," Current Pharmaceutical Biotechnology, vol. 4, No. 1, 2003, pp. 51-67 (Total 18 pages).
Corthésy, "Role of secretory immunoglobulin A and secretory component in the protection of mucosal surfaces," Future Microbiology, vol. 5, No. 5, 2010, pp. 817-829 (Total 14 pages).
Cottet et al., "Microaerophilic Conditions Permit to Mimic in Vitro Events Occurring during in Vivo Helicobacter pylori Infection and to Identify Rho/Ras-associated Proteins in Cellular Signaling," The Journal of Biological Chemistry, vol. 277, No. 37, Sep. 13, 2002, pp. 33978-33986 (10 pages).
Cripps et al., "Isolation of Human IgA and IgM from Normal Serum Using Polyethylene Glycol Precipitation and Affinity Chromatography," Journal of Immunological Methods, vol. 57, 1983, pp. 197-204.
Crottet et al., "Mapping the Interaction Between Murine IgA and Murine Secretory Component Carrying Epitope Substitutions Reveals a Role of Domains II and III in Covalent Binding to IgA," The Journal of Biological Chemistry, vol. 274, No. 44, Oct. 29, 1999, pp. 31456-31462 (Total 8 pages).
Crottet et al., "Secretory Component Delays the Conversion of Secretory IgA into Antigen-Binding Competent $F(ab')_2$: A Possible Implication for Mucosal Defense," The Journal of Immunology, vol. 161, 1998, pp. 5445-5453 (Total 10 pages).
Deshmane et al., "Monocyte Chemoattractant Protein-1 (MCP-1): An Overview," Journal of Interferon and Cytokine Research, vol. 29, No. 6, 2009, pp. 313-326.
Dewhirst et al., "The Human Oral Microbiome," Journal of Bacteriology, vol. 192, No. 19, Oct. 2010 (Published ahead of print on Jul. 23, 2010), pp. 5002-5017 (Total 17 pages).
Doellgast et al., "Purification of Human IgA by Salt-Mediated Hydrophobic Chromatography," Immunochemistry, vol. 13, 1976, pp. 135-139.
Donadoni et al., "Setting of Methods for Analysis of Mucosal Antibodies in Seminal and Vaginal Fluids of HIV Seropositive Subjects from Cambodian and Italian Cohorts," PLoS ONE, Issue 5, No. 3, Mar. 29, 2010, e9920, pp. 1-16.
Donnelly et al., "Antimicrobial therapy to prevent or treat oral mucositis," The Lancet Infectious Diseases, vol. 3, Jul. 2003, pp. 405-412.
Eibl et al., "Prevention of Necrotizing Enterocolitis in Low-Birth-Weight Infants by IgA-IgG Feeding," The New England Journal of Medicine, vol. 319, No. 1, Jul. 7, 1988, pp. 1-7.
Eldika et al., "Role of nontypeable Haemophilus Influenzae in exacerbations and progression of chronic obstructive pulmonary disease," Current Opinion in Pulmonary Medicine, vol. 12, 2006, pp. 118-124.
Elting et al., "The Burdens of Cancer Therapy: Clinical and Economic Outcomes of Chemotherapy-Induced Mucositis," Cancer, vol. 98, No. 7, Oct. 1, 2003, pp. 1531-1539.
Ertugrul et al., "Comparison of CCL28, interleukin-8, interleukin-1 β and tumor necrosis factor-alpha in subjects with gingivitis, chronic periodontitis and generalized aggressive periodontitis," Journal of Periodontal Research, vol. 48, 2013, pp. 44-51.
European Communication Pursuant to Article 94(3) EPC dated Apr. 23, 2014, in European Patent Application No. 11794757.2.
European Communication Pursuant to Article 94(3) EPC dated Dec. 15, 2014, in European Patent Application No. 11794757.2.
Extended European Search Report dated Aug. 8, 2012, for European Application No. 12158931.1.
Extended European Search Report for European Application No. 10194942.8 dated Oct. 28, 2011.

(56) References Cited

OTHER PUBLICATIONS

Extended European Search Report for European Application No. 12158939.4, dated Aug. 17, 2012.
Extended European Search Report dated Jul. 18, 2012, in European Patent Application No. 12158927.9.
Favre et al., "Simplified procedure to recover recombinant antigenized secretory IgA to be used as a vaccine vector," Journal of Chromatography B, vol. 786, 2003, pp. 143-151 (Total 10 pages).
Hammarström et al., "Systemic and Topical Immunoglobulin Treatment in Immunocompromised Patients," Immunological Reviews, No. 139, 1994, pp. 43-70.
Heiniger et al., "A Reservoir of Moraxella catarrhalis in Human Pharyngeal Lymphoid Tissue," The Journal of Infectious Diseases, vol. 196, Oct. 1, 2007 (Electronically published Aug. 30, 2007), pp. 1080-1087.
Helminen et al., "A Large, Antigenically Conserved Protein on the Surface of Moraxella catarrhalis Is a Target for Protective Antibodies," The Journal of Infectious Diseases, vol. 170, Oct. 1994, pp. 867-872.
Helminen et al., "A Major Outer Membrane Protein of Moraxella catarrhalis Is a Target for Antibodies That Enhance Pulmonary Clearance of the Pathogen in an Animal Model," Infection and Immunity, vol. 61, No. 5, May 1993, pp. 2003-2010 (Total 9 pages).
Hendrickson et al., "Lack of Association of Secretory Component with IgA in J Chain-Deficient Mice," The Journal of Immunology, vol. 157, 1996, pp. 750-754 (Total 6 pages).
International Preliminary Report on Patentability and Written Opinion of the International Searching Authority issued in International Application No. PCT/EP2013/054722 dated Sep. 18, 2014.
International Preliminary Report on Patentability and Written Opinion of the International Searching Authority dated Sep. 18, 2014, in International Application No. PCT/EP2013/054697.
International Preliminary Report on Patentability and Written Opinion of the International Searching Authority dated Sep. 18, 2014, in International Application No. PCT/EP2013/054698.
International Search Report and Written Opinion of the International Searching Authority (Forms PCT/ISA/220, PCT/ISA/210 and PCT/ISA/237) for International Application No. PCT/EP2011/072711 dated May 16, 2012.
International Search Report and Written Opinion of the International Searching Authority (Forms PCT/ISA/220, PCT/ISA/210, and PCT/ISA/237) for International Application No. PCT/EP2013/054722, dated May 7, 2013.
International Search Report and Written Opinion of the International Searching Authority dated Apr. 10, 2013, in International Application No. PCT/EP2013/054698.
International Search Report and Written Opinion of the International Searching Authority, dated Apr. 18, 2013, for International Application No. PCT/EP2013/054697.
Kanamaru et al., "IgA Fc receptor I signals apoptosis through the FcRγ ITAM and affects tumor growth," Blood, vol. 109, No. 1, Jan. 1, 2007 (Prepublished online: Sep. 25, 2006), pp. 203-211 (Total 10 pages).
Kobayashi et al., "Separation of Human sIgA1 and sIgA2 by Affinity Chromatography on the Jackfruit Lectin, Jacalin," Adv. Exp. Med. Biol., vol. 216B, 1987, pp. 1193-1197 (Total 6 pages).
Krajci et al., "Molecular Cloning of the Human Transmembrane Secretory Component (Poly-Ig Receptor) and its mRNA Expression in Human Tissues," Biochem. Biophys. Res. Comm., vol. 158, No. 3, Feb. 15, 1989, pp. 783-789.
Kunisawa et al., "A marvel of mucosal T cells and secretory antibodies for the creation of first lines of defense," CMLS Cellular and Molecular Life Sciences, vol. 62, 2005, pp. 1308-1321.
Leibl et al., "Isolation of Human Serum IgA Using Thiophilic Adsorption Chromatography," Protein Expression and Purification, vol. 6, 1995, pp. 408-410.
Leung et al., "Charge-dependent binding of polymeric $IgA_1$ to human mesangial cells in IgA nephropathy," Kidney International, vol. 59, 2001, pp. 277-285.
Liu et al., "CXCL10/IP-10 in infectious diseases pathogenesis and potential therapeutic implications," Cytokine & Growth Factor Reviews, vol. 22, 2011 (Available online Jul. 29, 2011), pp. 121-130.
Luellau et al., "Development of a downstream process for the isolation and separation of monoclonal immunoglobulin A monomers, dimers and polymers from cell culture supernatant," Journal of Chromatography A, vol. 796, 1998, pp. 165-175.
Lüllau et al., "Antigen Binding Properties of Purified Immunoglobulin A and Reconstituted Secretory Immunoglobulin A Antibodies," The Journal of Biological Chemistry, vol. 271, No. 27, Jul. 5, 1996, pp. 16300-16309.
Lüllau et al., "Development of a bioprocess for murine dimeric IgA production," Biotechnology Techniques, vol. 12, No. 6, Jun. 1998, pp. 425-430.
MacPherson et al., "The immune geography of IgA induction and function," Mucosal Immunology, vol. 1, No. 1, Jan. 2008, pp. 11-22.
Meier et al., "Moraxella catarrhalis strains with reduced expression of the UspA outer membrane proteins belong to a distinct subpopulation," Vaccine, vol. 23, 2005 (Available online Nov. 10, 2004), pp. 2000-2008.
Meier et al., "Salivary Antibodies Directed against Outer Membrane Proteins of Moraxella catarrhalis in Healthy Adults," Infection and Immunity, vol. 71, No. 12, Dec. 2003, pp. 6793-6798 (Total 7 pages).
Monteiro et al., "IgA Fc Receptors," The Annual Review of Immunology, vol. 21, 2003 (First published online as a Review in Advance on Jan. 28, 2003), pp. 177-204 (Total 34 pages).
Mose et al., "Can Prophylactic Application of Immunoglobulin Decrease Radiotherapy-Induced Oral Mucositis?" American Journal of Clinical Oncology, vol. 20, Issue 4, Aug. 1997, pp. 407-411 (14 pages total).
Moura et al., "Identification of the Transferrin Receptor as a Novel Immunoglobulin (Ig)A1 Receptor and Its Enhanced Expression on Mesangial Cells in IgA Nephropathy," The Journal of Experimental Medicine, vol. 194, No. 4, Aug. 20, 2001, pp. 417-425.
Murphy et al., "Isolation of the outer membrane of Branhamella catarrhalis," Microbial Pathogenesis, vol. 6, 1989, pp. 159-174.
Nicoletti et al., "A rapid and simple method for measuring thymocyte apoptosis by propidium iodide staining and flow cytometry," J. Immunol. Methods, vol. 139, 1991, pp. 271-279.
Nitschmann et al., "107. Vereinfachtes Verfahren zur Gewinnung von humanem Albumin und γ-Globulin aus Blutplasma mittels Alkoholfällung," Helvetica Chimica Acta., vol. 37, 1954, pp. 866-873, including English summary.
Oncley et al., "The separation of the Antibodies, Isoagglutinins, Prothrombin, Plasminogen, and β1-Lipoprotein into Subfractions of Human Plasma," J. Am. Chem. Soc., vol. 71, Feb. 1949, pp. 541-550.
Oral Cancer Foundation, "Prevention and Treatment of Oral Mucositis in Cancer Patients," Best Practice, Evidence Based Practice Information Sheets for Health Professionals, vol. 2, Issue 3, 1998, pp. 1-6 (2 pages provided).
Pasquier et al., "Identification of FcαRI as an Inhibitory Receptor that Controls Inflammation: Dual Role of FcRy ITAM," Immunity, vol. 22, Jan. 2005, pp. 31-42.
Pejaudier et al., "Preparation of Human IgA as By-Product of Routine Fractionation," Vox Sang., vol. 23, 1972, pp. 165-175.
Pleass et al., "Identification of Residues in the CH2/CH3 Domain Interface of IgA Essential for Interaction with the Human FcαReceptor (Fc αR) CD89," J. Biol. Chem, vol. 274, No. 33, Aug. 13, 1999, pp. 23508-23514 (Total 9 pages).
Plevová et al., "Intravenous Immunoglobulin as Prophylaxis of Chemotherapy-Induced Oral Mucositis," Correspondence, Journal of the National Cancer Institute, vol. 89, No. 4, Feb. 19, 1997, pp. 326-327, XP002680345.
Ponka et al., "The transferrin receptor: role in health and disease," The International Journal of Biochemistry & Cell Biology, vol. 31, 1999, pp. 1111-1137.
Que et al., "Fibrinogen and fibronectin binding cooperate for valve infection and invasion in *Staphylococcus aureus* experimental endocarditis," The Journal of Experimental Medicine, vol. 201, No. 10, May 16, 2005, pp. 1627-1635.

(56) References Cited

OTHER PUBLICATIONS

Ratner et al., "Synergistic proinflammatory responses induced by polymicrobial colonization of epithelial surfaces," Proceedings of the National Academy of Sciences, vol. 102, No. 9, Mar. 1, 2005, pp. 3429-3434.
Rincon, "Interleukin-6: from an inflammatory marker to a target for inflammatory diseases," Trends in Immunology, vol. 33, No, 11, Nov. 2012, pp. 571-577.
Rindisbacher et al., "Production of Human Secretory Component with Dimeric IgA Binding Capacity Using Viral Expression Systems," The Journal of Biological Chemistry, vol. 270, No. 23, Jun. 9, 1995, pp. 14220-14228 (Total 10 pages).
Roque-Barreira et al., "Jacalin: An IgA-Binding Lectin," The Journal of Immunology, vol. 134, No. 3, Mar. 1985, pp. 1740-1743.
Ryu et al., "Therapeutic Effects of Recombinant Human Epidermal Growth Factor (rhEGF) in a Murine Model of Concurrent Chemo- and Radiotherapy-Induced Oral Mucositis," Journal of Radiation Research, vol. 51, 2010, pp. 595-601.
Salamone et al., "Promotion of Neutrophil Apoptosis by TNF-$\alpha^1$," J. Immunol, vol. 166, 2001, pp. 3476-3483 (Total 9 pages).
Schedler et al., "Treatment of radiogenic mucositis in patients with head and neck tumors with polyvalent intramuscular immunoglobulin," Tumor Diagnostik und Therapie, vol. 15, No. 5, 1994, pp. 184-191,XP009161354, along with un English summary.
Schettini et al., "Stimulation of neutrophil apoptosis by immobilized IgA," Journal of Leukocyte Biology, vol. 72, Oct. 2002, pp. 685-691.
Singapore Invitation to Respond to Written Opinion issued Oct. 30, 2014, in Singapore Patent Application No. 2013041322.
Sonis, "Mucositis as a biological process: a new hypothesis for the development of chemotherapy-induced stomatotoxicity," Oral Oncology, vol. 34, 1998, pp. 39-43.
Sonis, "Mucositis: The impact, biology and therapeutic opportunities of oral mucositis," Oral Oncology, vol. 45, 2009 (Available online Oct. 13, 2009), pp. 1015-1020.
Spaniol et al., "Outer membrane protein UspA1 and lipooligosaccharide are involved in invasion of human epithelial cells by Moraxella catarrhalis," Microbes and Infection, vol. 10, 2008 (Available online Oct. 2, 2007), pp. 3-11.
Spielberger et al., "Palifermin for Oral Mucositis after Intensive Therapy for Hematologic Cancers," The New England Journal of Medicine, vol. 351, No. 25, Dec. 16, 2004, pp, 2590-2598.
Steinbuch et al., "The isolation of IgG from Mammalian Sera with the Aid of Caprylic Acid," Archives of Biochemistry and Biophysics, vol. 134, 1969, pp. 279-284.
Stokman et al., "Oral mucositis and selective elimination of oral flora in head and neck cancer patients receiving radiotherapy: a double-blind randomised clinical trial," British Journal of Cancer, vol. 88, No. 7, 2003, pp. 1012-1016.
Suzuki et al., "Autocrine production of epithelial cell-derived neutrophil attractant-78 induced by granulocyte colony-stimulating factor in neutrophils," Blood, vol. 99, No. 5, Mar. 1, 2002, pp. 1863-1865.
Takeshita et al., "Intravenous immunoglobulin preparations promote apoptosis in lipopolysaccharide-stimulated neutrophils via an oxygen-dependent pathway in vitro," APMIS, Vol, 113, 2005, pp. 269-277.
The Human Microbiome Project Consortium, "Structure, function and diversity of the healthy human microbiome," Nature, vol. 486, Jun. 14, 2012, pp. 207-214.
Van Der Steen et al., "Immunoglobulin A: FcαRI Interactions Induce Neutrophil Migration Through Release of Leukotriene B4," Basic-Alimentary Tract, Gastrogenterology, vol. 137, No. 6, Dec. 2009, pp. 2018-2029.e3.
Von Gunten et al., "Siglec-9 transduces apoptotic and nonapoptotic death signals into neutrophils depending on the proinflammatory cytokine environment," Blood, vol. 106, No. 4, Aug. 15, 2005 (Prepublished online: Apr. 12, 2005), pp. 1423-1431 (Total 10 pages).
Watkins et al., "Attenuation of radiation- and chemoradiation-induced mucositis using gamma-D-glutamyl-L-tryptophan (SCV-07)," Oral Diseases, vol. 16, 2010, pp. 655-660.
Wheeler et al., "Immune Components of Colostrum and Milk—A Historical Perspective," Journal of Mammary Gland Biological Neoplasia, vol. 12, 2007 (Published online Nov. 9, 2007), pp. 237-247 (Total 12 pages).
Wiersma et al., "Structural and Functional Analysis of J Chain-Deficient IgM," J. Immunol., vol. 160, 1998, pp. 5979-5989 (Total 12 pages).
Wijers et al., "Mucositis reduction by selective elimination of oral flora in irradiated cancers of the head and neck: A placebo-controlled double-blind randomized study," International Journal of Radiation Oncology Biology Physics, vol. 50, No. 2, 2001, pp. 343-352.
Wörn et al., "Stability Engineering of Antibody Single-chain Fv Fragments," J. Mol. Biol, vol. 305, 2001, pp. 989-1010.
Zuercher et al., "Plasma-derived immunoglobulins," Principles of Immunopharmacology: 3rd revised and extended edition, 2011, pp. 271-301.
Atassi et al., "Molecular Immunology," A Textbook, Marcel Dekker, Inc., Aug. 31, 1988, pp. 207-210 (Total 6 pages).
Balsari et al., "Topical Administration of a Doxorubicin-specific Monoclonal Antibody Prevents Drug-induced Mouth Apoptosis in Mice," British Journal of Cancer, vol. 85, No. 12, 2001, pp. 1964-1967.
Bessen et al., "Passive Acquired Mucosal Immunity to Group A *Streptococci* by Secretory Immunoglobulin A," Journal of Experimental Medicine, vol. 167, No. 6, Jun. 1, 1988, pp. 1945-1950.
Boullier et al., "Secretory IgA-Mediated Neutralization of Shigella flexneri Prevents Intestinal Tissue Destruction by Down-Regulating Inflammatory Circuits," The Journal of Immunology, vol. 183, No. 9, 2009, pp. 5879-5885.
Brandtzaeg, "Mucosal Immunity: Integration between Mother and the Breast-fed Infant," Vaccine, vol. 21, 2003, pp. 3382-3388.
Cheng et al., "Evaluation of an Oral Care Protocol Intervention in the Prevention of Chemotherapy-induced Oral Mucositis in Paediatric Cancer Patients," European Journal of Cancer, vol. 37, 2001, pp. 2056-2063.
Chinese Office Action and Chinese Search Report, dated Oct. 24, 2016, for Chinese Application No. 201380013075.7 (English translation only).
CSL Behring, "Company Core Data Sheet for Beriglobin," Sep. 16, 2015, together with an English translation thereof, 17 pages total.
De Wit et al., "Structure of the gene for the human myeloid IgA Fc receptor (CD89)," The Journal of Immunology, vol. 155, 1995, pp. 1203-1209 (Total 8 pages).
Delacroix et al., "Changes in Size, Subclass, and Metabolic Properties of Serum Immunoglobulin A in Liver Diseases and in Other Diseases with High Serum Immunoglobulin A," J Clin. Invest., vol. 71, Feb. 1983, pp. 358-367.
Delacroix et al., "Selective Transport of Polymeric Immunoglobulin A in Bile," J Clin. Invest., Vol, 70, Aug. 1982, pp. 230-241.
English translation of Russian Office Action, dated Nov. 12, 2015, for Russian Application No. 2013132220.
English translation of the Japanese Office Action, dated Nov. 1, 2016, for Japanese Application No. 2014-560392.
English translation of the Japanese Office Action, dated Oct. 25, 2016, for Japanese Application No. 2014-560387.
Fluckiger et al., "Immunoglobulins Inhibit Adherence and Internalization of *Streptococcus pyogenes* to Human Pharyngeal Cells," Advances in Experimental Medicine and Biology, vol. 418, 1997, pp. 909-911.
Fluckiger et al., "Immunoglobulins to Group A *Streptococcal* Surface Molecules Decrease Adherence to and Invasion of Human Pharyngeal Cells," Infection and Immunity, vol. 66, No. 3, Mar. 1998, pp. 974-979.
Frese et al., "Maximizing Mouse Cancer Models," Nature Reviews, vol. 7, Sep. 2007, pp. 645-658.
Ge Healthcare Life Sciences, "Mono Q 5/50 GL," Product Data Sheet, Product Code: 17/5166-01, 2016, 1 page.
Gonzalez-Quintela et al., "Serum levels of immunoglobulins (IgG, IgA, IgM) in a general adult population and their relationship with

(56) References Cited

OTHER PUBLICATIONS alcohol consumption, smoking and common metabolic abnormalities," Clinical and Experimental Immunology, vol. 151, 2007, pp. 42-50.
Himi et al., "Immune Barrier Changes in Patients with Head and Neck Cancer," Stomata-pharyngology, vol. 6, No. 2, 1994, pp. 71-77, with an English abstract.
Janeway Jr, et al., "Immunobiology," 3rd edition, Garland Publishing Inc., 1997, pp. 8:18-8:19 and 9:19-9:20.
Japanese Office Action for Japanese Application No. 2013-543743 dated Dec. 1, 2015, with an English translation.
Japanese Office Action, dated Nov. 15, 2016, for Japanese Application No. 2014-560388, with an English translation.
Johansen et al., "Role of J Chain in Secretory Immunoglobulin Formation," Scandinavian Journal of Immunology, vol. 52, 2000, pp. 240-248.
Karolewska et al., "Antibacterial potential of saliva in children with leukemia," Oral Surgery, Oral Medicine, Oral Pathology, Oral Radiology, and Endodontics, vol. 105, No. 6, Jun. 2008, pp. 739-744.
Keefe et al., "Updated Clinical Practice Guidelines for the Prevention and Treatment of Mucositis," Cancer, vol. 109, No. 5, Mar. 1, 2007, pp. 820-831.
Leibl et al., "Method for the Isolation of Biologically Active Monomeric Immunoglobulin A from a Plasma Fraction," Journal of Chromatography B, vol. 678, 1996, pp. 173-180.
Lindh et al., "Binding of Secretory Component to Human Immunoglobulin M," Eur. J. Biochem., vol. 62, 1976, pp. 271-278.
Lüer et al., "Topical Curcumin Can Inhibit Deleterious Effects of Upper Respiratory Tract Bacteria on Human Oropharyngeal Cells in Vitro: Potential Role for Patients with Cancer Therapy Induced Mucositis?" Support Care Cancer, vol. 19, 2011 (Published online: May 14, 2010), pp. 799-806.
Malmquist et al., "Characterization of the Influence of Displacing Salts on Retention in Gradient Elution Ion-exchange Chromatography of Proteins and Peptides," Journal of Chromatography, vol. 627, 1992, pp. 107-124 (Total 19 pages).
Morelli et al., "Oral Administration of Anti-Doxorubicin Monoclonal Antibody Prevents Chemotherapy-induced Gastrointestinal Toxicity in Mice," The Journal of Cancer Research, vol. 56, May 1, 1996, pp. 2082-2085 (Total 5 pages).
Phalipon et al., "Monoclonal Immunoglobulin A Antibody Directed against Serotype-specific Epitope of Shigella Flexneri Lipopolysaccharide Protects against Murine Experimental Shigellosis," J. Exp. Med., Vol, 182, Sep. 1, 1995, pp. 769-778.
Qingyi et al., "Biochemical Experiments of Food Products," South China University of Technology Press, Feb. 1, 2012, pp. 24-26 and 30 (Total 6 pages).
Saito et al., "Biological Activity of Secretory IgA, Particularly antibacterial immunity as an example," J. Stomatol. Soc. Jpn., Apr. 26, 1976, vol. 43, No. 2, pp. 107-112.
Sørensen et al., "Structural requirements for incorporation of J chain into human IgM and IgA," International Immunology, vol. 12, No. 1, 2000, pp. 19-27.
Steinbuch et al. "Isolement de L'Immunoglobuline IgG Du Plasma Humain a L'Aide de L'Acide Caprylique," Rev. Franc. Etudes Clin. et Biol., vol. XIV, 1969, pp. 1054-1058, with English abstract on p. 1057.
Teschner et al., "A New Liquid, Intravenous Immunoglobulin Product (IGIV 10%) Highly Purified by a State-of-the-art Process," Vox Sanguinis, vol. 92, 2007 (Published online Oct. 24, 2006), pp, 42-55 (Total 15 pages).
Walsh, "Proteins Biochemistry and Biotechnology," John Wiley & Sons, Mar. 2006, p. 82 (Total 3 pages).
Wright et al, "Neutrophil Function in Inflammation and Inflammatory Diseases," Rheumatology, vol. 49, 2010 (Advanced Access publication Mar. 24, 2010), pp. 1618-1631.
U.S. Office Action issued in U.S. Appl. No. 15/384,140 dated Sep. 14, 2017.
European Office Communication Enclosing Third Party Observation for European Application No. 13708787.0 dated Apr. 7, 2017.
Stubbe et al., "Polymeric IgA Is Superior to Monomeric IgA and IgG Carrying the Same Variable Domain in Preventing Clostridium difficile Toxin A Damaging of T84 Monolayers," J Immunol, vol. 164, No. 4, Feb. 15, 2000, pp. 1952-1960.

\* cited by examiner

IgM and IgA from plasma bind to *C. difficile* clinical isolate (dot blot assay)

Figure 4

IVIg (Privigen), IgM and IgA from plasma neutralize *C. difficile* toxin B

Toxin B concentration: 0.02 µg/ml

Prevention of recurrence of *C. difficile* infection with
IgA F5 and IgA F5 associated with recSC
after treatment of primary infection with vancomycin

PREVENTION OF INFECTION

The invention relates to compositions and methods to prevent enteric infection in a subject at risk of such infection. In particular, the invention relates to the prevention of recurrence of infection by *Clostridium difficile*.

INTRODUCTION

Acute and chronic gastro-intestinal (GI) infection with bacterial, viral or eukaryotic pathogens is among the major causes for illness worldwide. Outbreaks at various scales (local to pandemic) are common in the general population, but especially in subjects with compromised immunity (e.g. newborns, the elderly, patients with primary or secondary immunodeficiency) GI infection may be particularly severe and become chronic. The main therapeutic approach against bacterial GI infection are antibiotics, however, efficacy of many currently used antibiotics is decreasing due to the increasing rate of resistance to multiple antibiotics in many strains.

*C. difficile* is an anaerobic, gram positive, spore-forming *bacillus* that was first isolated in 1935 from the stool of healthy neonates (Kelly, C P & LaMont, J T (2008) N Engl J Med 359: 1932-40). It was not until 1978 that the association between toxins released by this organism (toxins A and B) and antibiotic-associated pseudomembranous colitis was first reported (Bartlett, J G et al (1978) N Engl J Med 298: 531-4). Knowledge of the epidemiology, pathogenesis and treatment of *C. difficile* infection (CU) has increased substantially during the past three decades (Kelly, C P & LaMont, J T (2008) N Engl J Med 359: 1932-40). However, this increased knowledge has not led to a decline in disease frequency or severity. To the contrary, *C. difficile* has now surpassed MRSA as the most frequent bacterial cause of nosocomial infection (Miller, B A et al (2011) Infect Control Hosp Epidemiol 32: 387-90) and CDI has become the leading recognized cause of nosocomial infectious diarrhea in the developed world. Furthermore, in the US, and elsewhere, the incidence of CDI and mortality rates from the disease have increased dramatically since 2000 (Kelly, C P & LaMont, J T (2008) N Engl J Med 359: 1932-40). These increases are fueled in part by the emergence of hypervirulent strains with wide-ranging antibiotic resistance (2009, Int J Antimicrob Agents 33 Suppl 1: S1-56) as well as the appearance of toxin-hyperproducers e.g. PCR Ribotype 027 (Kuijper E J et al (2006) Clin Microbiol Infect 12, Suppl 6: 2-18).

Treatment with metronidazol and vancomycin is the current standard of care and indeed most patients with CDI are successfully treated with this approach. However, upon successful treatment of the primary infection, roughly 25% of patients experience recurrence of disease. The recurrence rate can be as high as 65% in patients with a history of previous CDI (Kelly, C P & LaMont, J T (2008) N Engl J Med 359: 1932-40; Hu M Y et al (2009) 136: 1206-14). Multiple recurrences are frequently observed, and patients with more than 10 episodes have been reported (Kelly, C P & LaMont, J T (2008) N Engl J Med 359: 1932-40; Hu M Y et al (2009) 136: 1206-14). Recurrence typically occurs 1-3 weeks after resolution of primary infection, but also late onset of recurrence after 2 month or more has been observed (Kelly, C P & LaMont, J T (2008) N Engl J Med 359: 1932-40; Hu M Y et al (2009) 136: 1206-14). Recurrent/chronic CDI is associated with prolonged hospitalization, increased costs and significant mortality rates of 6-16% (Kelly, C P & LaMont, J T (2008) N Engl J Med 359: 1932-40; Hu M Y et al (2009) 136: 1206-14). Furthermore, severe complications, such as development of toxic megacolon have been reported, highlighting the strong inflammatory component inherent to chronic/recurrent *C. difficile* infection.

Different approaches have been suggested to address the problem of recurrence of CDI. They include longer treatment cycles with vancomycin or metronidazol, tapered and pulsed schedules of vancomycin, other antimicrobials (e.g. fidaxomicin or rifaximin), use of toxin-binding agents such as cholestyramine, use of probiotics, e.g. *Saccharomyces* or *Lactobacillus*, fecal transplantation and immunotherapy (Surawicz, C M & Alexander, J. (2011) Nat Rev Gastroenterol Hepatol 8: 330-9). Immune approaches attempted so far included vaccination, the use of anti-*Clostridium difficile* colostral or whey protein from cows immunized with *C. difficile* and passive immunization with intravenous immunoglobulin (IVIg) (Surawicz, C M & Alexander, J. (2011) Nat Rev Gastroenterol Hepatol 8: 330-9). Despite some encouraging studies in a limited number of patients neither specific cow antibodies nor polyclonal IVIg has become a commonly used treatment. In addition, monoclonal antibodies specific for toxins A and B from *C. difficile* are currently in clinical development with some initial success in prevention of recurrence (Lowy, I. et al (2010) N Engl J Med 362: 197-205). Nevertheless, none of these approaches to management of CDI has so far proven to be robustly successful. One possible explanation for this finding is the fact that most of the treatment approaches target either *C. difficile* bacteria (e.g. antibiotics) or the toxins produced by them (e.g. monoclonal antibodies). Consequently recurrence of CDI is still a significant and unsolved clinical and therapeutic problem.

Consequently there is a need for more effective ways to prevent enteric infection in patients at risk of such infections. In particular, there is a need for better treatments to prevent a recurrence of *C. difficile* infection.

The inventors have now surprisingly found that an infection by an enteric pathogen can be prevented in a subject at risk of infection with a composition comprising secretory component and immunoglobulin. One aspect of the invention is therefore a composition comprising secretory component and immunoglobulin for use in the prevention of an infection by an enteric pathogen in a subject at risk of infection, wherein the composition is not obtained from milk.

Preferably the enteric pathogen is bacterial, more preferably it is a toxin-releasing bacterium and/or a spore-forming bacterium. Most preferably, the bacterium is *Clostridium difficile*, and the subject at risk of infection is a patient after having received antibiotic treatment for a primary *Clostridium difficile* infection.

The secretory component comprised in the composition may be recombinant secretory component, preferably secretory component produced in a mammalian cell line. The secretory component may also be from a natural source, preferably from milk, saliva or mucus. Preferably the secretory component is human. More preferably, it is the extracellular portion of the human polyclonal immunoglobulin receptor pIgR.

The immunoglobulin comprised in the composition comprises IgA, preferably it also comprises a J chain-containing IgA. Preferably, it is derived from blood or components thereof, even more preferably, it is derived from plasma. Most preferably, the immunoglobulin comprises J chain-containing dimeric IgA. Most preferably, the immunoglobulin is human IgA.

In another aspect of the invention, the immunoglobulin comprised in the composition comprises IgM, preferably J chain-containing IgM. Preferably, the IgM is human IgM.

In another aspect of the invention, the composition comprises IgA and IgM in combination.

Preferably, the immunoglobulin comprises anti-*Clostridium* IgA and/or IgM, and/or anti-*Clostridium* toxin IgA and/or IgM, and/or anti-*Clostridium* spore IgA and/or IgM.

The IgA is preferably polyclonal, but monoclonal IgA or a mixture of two or more monoclonal IgAs can also be used. The IgM is preferably polyclonal, but monoclonal IgM or a mixture of two or more monoclonal IgMs can also be used.

Preferably, the secretory component in the composition associates with J chain-containing IgA to form secretory-like IgA. However, the secretory component can also associate with IgM present in the composition.

Preferably, the composition is used for the prevention of enteric infection by oral administration in a subject at risk of infection.

In a preferred aspect of the invention, the administration is initiated after successful treatment of a *Clostridium difficile* infection by one or more antibiotics. The administration of the composition is preferably initiated up to 48 hours prior to the conclusion of the antibiotic treatment, or at or shortly after the conclusion of the antibiotic treatment. Preferably, the sequelae of recurrent infection, such as colitis, chronic inflammation of the intestine, are also prevented.

Preferably, the prevention of enteric infection also prevents sequelae of the enteric infection from occurring.

DETAILED DESCRIPTION OF THE INVENTION

As mentioned above, the inventors have surprisingly found that an infection by an enteric pathogen can be prevented in a subject at risk of infection with a composition comprising secretory component and immunoglobulin. The invention therefore provides new compositions for use in the prevention of enteric infections. One aspect of the invention is therefore a composition comprising secretory component and immunoglobulin for use in the prevention of an infection by an enteric pathogen in a subject at risk of infection, wherein the composition is not obtained from milk.

Preferably the enteric pathogen is bacterial, more preferably it is a toxin-releasing bacterium and/or a spore-forming bacterium. Examples of bacteria that may cause enteric infections are various species of *Salmonella, Shigella, Campylobacter, Escherichia coli, Vibrio cholera, Enterococcus* and anaerobic streptococci. Preferably, the bacterium is *Clostridium difficile*, and the subject at risk of infection is a patient after having received antibiotic treatment for a primary *Clostridium difficile* infection.

The enteric pathogen may also be fungal (e.g. *Histoplasma*) or viral (e.g. Norovirus), or it could be a parasite (e.g. *Giardia, Cryptosporidium*).

The term "secretory component" as used herein refers to a protein that specifically binds to J-chain-containing immunoglobulin, and is related to or derivable from or identical to an extracellular portion of the polymeric immunoglobulin receptor (pIgR), preferably a mammalian pIgR, more preferably a primate pIGR, most preferably a human pIgR. Preferably, the secretory component confers increased stability to the J-chain containing immunoglobulin. The secretory component comprised in the composition may be recombinant secretory component, preferably secretory component produced in a mammalian cell line. Secretory component in its traditional, narrow meaning (referred to as "natural secretory component" herein) is the extracellular portion of the polymeric immunoglobulin receptor (pIgR), which usually gets associated during secretion with dimeric or polymeric IgA, or pentameric IgM, comprising a joining chain (J-chain). J chain-containing IgA or IgM binds to the polymeric immunoglobulin receptor at the basolateral surface of epithelial cells and is taken up into the cell by transcytosis. This receptor complex then transits through the cellular compartments before being transported to the luminal surface of the epithelial cells. The transcytosed IgA-pIgR or IgM-pIgR complex is then released through proteolysis, and part of the polymeric immunoglobulin receptor (pIgR), referred to as the natural secretory component, stays associated with the J chain-containing IgA or IgM, releasing secretory IgA or secretory IgM. However, there is evidence that reverse transcytosis of IgA, i.e. from the luminal surface to the basolateral surface, can also take place.

The human pIgR is cloned and sequenced, its sequence is available as SwissProt entry P01833, and shown in Seq ID NO: 1. Human pIgR is a glycoprotein with 764 amino acid residues, containing a signal peptide (residues 1 to 18), an extracellular part (residues 19 to 638), a transmembrane region (residues 639 to 661), and a cytoplasmic region (residues 662 to 764). Residues 19 to 603 are thought to associate with J chain-containing IgA as described above, and this part of this glycoprotein is usually referred to as the secretory component (referred to as "natural secretory component" herein).

The secretory component used in the composition of the invention may comprise any extracellular pIgR sequence that is capable of associating with J chain-containing IgA or IgM. For example, secretory component may comprise extracellular domains of pIgR from mammalian sources, e.g. from primates, cattle, horses, cats, dogs, rabbits, guinea pigs, rats or mice, or variants thereof. Functional hybrids of the extracellular domains from several mammalian species or variants thereof are also contemplated for use in the invention, e.g. prepared by fusing the immunoglobulin-like domains from different species into a secretory component-like protein. A functional secretory component may also be formed by fusing a selection of immunoglobulin-like domains normally present, e.g. rabbit secretory component is functional being composed of only domains 1, 4 and 5. Preferably, however, the extracellular portion of the human pIgR, in particular the natural human secretory component, or functional variants thereof, is used.

Therefore the secretory component used in the composition of the invention preferably comprises residues 19 to 603 of SEQ ID NO: 1 or functional variants thereof. Functional variants may include deletions, insertions, and/or substitutions, preferably substitutions are conservative substitutions, e.g. a basic amino acid residue is substituted for another basic amino acid, a hydrophobic amino acid is substituted for another hydrophobic amino acid, etc. The variant secretory component is at least 50% identical in sequence to residues 19 to 603 of SEQ ID NO: 1, preferably at least 55%, 60%, 65%, 70%, 75%, 80%, more preferably at least 85% or even 90%, even more preferably at least 92%, 94%, 95%, 97%, 98%, or even 99% identical to residues 19 to 603 of SEQ ID NO: 1. Most preferably, the secretory component comprises or even consists of residues 19 to 603 of SEQ ID NO: 1.

The skilled person is well aware how to produce the secretory component by recombinant techniques. An example of expression of human secretory component in CHO cells has been described by Phalipon et al (Phalipon A et al (2002) Immunity 17:107-115), but the invention is not limited to secretory component produced by this system. For example, the desired cDNA sequence can be produced synthetically or cloned via RT-PCR, using RNA isolated from cells or tissue expressing pIgR as template. The cDNA can then be inserted into a mammalian expression vector such as pcDNA3—many alternative expression vectors are available and are well known to the skilled person. The recombinant expression vector will then be introduced into a suitable host cell line, such as CHO, Cos, HEK293, or BHK. Other cell lines are available and can also be used. Methods for introducing such vectors into a cell line include lipofection, electroporation and other techniques well known to the skilled person. Usually cells harboring the expression vector and expressing the protein of interest are then selected and cloned. Viral expression systems can also be used, for example, vaccinia virus can be used to express proteins at high levels in mammalian cells, baculovirus expression systems can be used to express proteins at high levels in insect cells. Yeast or bacterial expression systems can also be envisaged, and such expression systems are known to the skilled person. Plant expression systems can also be used and are known to the skilled person.

The secretory component or variant thereof used in the composition of the invention may also comprise a tag, such as a hexa-Histidine tag, which can aid in the purification of the resulting protein. If such a tag is attached via a cleavable linker, the tag may be cleaved off prior to use in the invention. Similarly, the secretory component may be produced as a fusion protein. Again, a cleavable linker may be used so that the fusion partner may be cleaved off the secretory component prior to use in the invention.

The skilled person can then purify the expressed protein with standard methods.

The secretory component may also be obtained from a natural source, preferably from milk, saliva or mucus. Preferably the secretory component is of human origin, but secretory component from other species can also be used in the invention.

The immunoglobulin comprised in the composition comprises IgA, preferably a J chain-containing IgA, IgM or combinations thereof. Preferably, it is derived from blood or components thereof, more preferably, it is derived from plasma, even more preferably it is obtained from pools of plasma from multiple donors. Most preferably, the immunoglobulin comprises J chain-containing dimeric IgA. Most preferably, the immunoglobulin, e.g. the IgA, is human IgA. Additionally or alternatively, the composition may comprise IgM, preferably J chain-containing pentameric IgM.

IgA is an antibody that is found in blood and derivatives thereof, but also on mucosal surfaces as it plays a critical role in mucosal immunity. Human IgA has two subclasses, IgA1 and IgA2. In serum, it exists mainly in monomeric form, but dimeric and polymeric IgA can also be found. The predominant IgA subclass found in serum is IgA1. Dimeric and polymeric IgA is often complexed with a joining chain (J chain), which is produced by IgA-secreting cells and presumably complexed with two IgA molecules prior to release from these cells.

At mucosal surfaces and generally in secretions (e.g. milk, tears, saliva, mucus), J chain-containing dimers or polymers complexed with natural secretory component are found. IgA2 is generally more prominent than in blood. The natural secretory component is added to J chain-containing IgA through the secretion mechanism as described above. The resulting complex is called secretory IgA. It has been found that secretory IgA is less prone to proteolysis than other forms of IgA.

IgM is mostly found in blood, i.e. plasma or serum, as a J chain-containing pentamer, or a hexamer. It is often the first line of defense against pathogens. In a healthy individual, the concentration of IgM in secretions is rather low. However, in IgA-deficient patients, it can take over IgA's role on mucosal surfaces.

Preferably, the composition of the invention comprises IgA, IgM or combinations thereof that bind(s) the enteric pathogen and/or a toxin it produces and/or a spore if the pathogen is spore-forming. More preferably, the composition comprises anti-pathogen IgA and/or IgM, and anti-toxin IgA and/or IgM, even more preferably, the composition additionally comprises anti-spore IgA and/or IgM in case of a spore-forming pathogen.

Preferably, the composition of the invention comprises anti-*Clostridium*-IgA and/or IgM, and/or anti-*Clostridium* toxin IgA and/or IgM, and/or anti-spore IgA and/or IgM. More preferably, the immunoglobulin comprises anti-*Clostridium*-IgA and/or IgM and anti-toxin IgA, even more preferably, the immunoglobulin comprises anti-toxin A IgA and anti-toxin B-IgA. Most preferably, the immunoglobulin also comprises anti-spore IgA and/or IgM.

The IgA is preferably polyclonal, but monoclonal IgA or a mixture of two or more monoclonal IgAs can also be used. The same applies to IgM.

Preferably, the secretory component in the composition associates with J chain-containing IgA to form secretory-like IgA. However, the secretory component can also associate with IgM that may be present in the composition to form secretory-like IgM. Thus, the term "secretory-like" IgA/IgM refers to J chain-containing IgA or IgM, combined with secretory component in vitro.

The inventors have surprisingly found that plasma-derived immunoglobulin mixed with secretory component leads to the formation of secretory-like IgA and/or secretory-like IgM, i.e. J chain-containing IgA dimers, tetramers or other polymer forms or J chain-containing IgM pentamers complexed with secretory component, that will provide effective protection from infection or recurrence of infection in the gut environment. Surprisingly, the J chain-containing IgA dimers, tetramers or other polymer forms, or the J chain-containing IgM pentamers, do not require purification from plasma prior to mixing with secretory component. However, it is preferred to enrich the composition for such J chain-containing IgA and/or J chain-containing IgM prior to mixing with the secretory component. Preferably, the J chain-containing IgA comprises at least 5%, more preferably at least 10%, even more preferably at least 20%, 30%, 50%, most preferably at least 70% of the immunoglobulin of the composition. In another preferred aspect of the invention, the J chain-containing IgM pentamers comprise at least 5%, more preferably at least 10%, even more preferably at least 120%, 30%, 50%, most preferably at least 70% of the immunoglobulin of the composition. In a further preferred aspect of the invention, the composition comprises a mixture of J chain-containing IgA and J chain-containing IgM, wherein the ratio of IgA to IgM is between 1:20 and 20:1, preferably 1:10 and 10:1, preferably between 1:5 and 5:1, more preferably between 1:2 and 2:1.

Preferably, the composition is used for the prevention of enteric infection by oral administration in a subject at risk of infection. However, other forms of administration, such as anal delivery or enteric delivery, are also included in the invention. The composition may be formulated with one or more pharmaceutically acceptable excipients, diluents, or carriers, it may additionally comprise stabilizers. The composition may be provided as a fluid, a syrup, a powder that may be reconstituted prior to administration, a capsule, pill or other suitable form. It may also be provided with a protective coating so that it is released in a defined region or regions of the gastro-intestinal tract.

In a preferred aspect of the invention, the administration is initiated after successful treatment of a *Clostridium difficile* infection by one or more antibiotics. The administration of the composition is preferably initiated up to 48 hours prior to the conclusion of the antibiotic treatment, or at or shortly after the conclusion of the antibiotic treatment. Preferably, the composition of the invention prevents recurrence of a *Clostridium difficile* infection for at least one month after the final administration, more preferably for at least two months, even more preferably for at least 3 months, most preferably for at least 6 months, a year or even longer. The composition of the invention is effective for the prevention of recurrence of a *C. difficile* infection involving the same strain of *C. difficile* as the strain that caused the previous infection, preferably, it is effective for the prevention of recurrence of a *C. difficile* infection involving the same or a different strain of *C. difficile* that caused the previous infection, or more than one strain of *C. difficile*, be it hospital or non-hospital-derived strains. Preferably, it is also effective for the prevention of possible sequelae of recurrent *C. difficile* infection, such as colitis or chronic inflammation of the intestine.

The composition can be administered in multiple doses per day, preferably less than four times per day, more preferably less than three times, even more preferably less than twice, most preferably once a day or even less frequently.

An enteric infection is a disease of the intestine caused by any infection. Symptoms are usually selected from diarrhea, abdominal discomfort, nausea and vomiting, and anorexia, and combinations thereof. Diarrhea and vomiting can lead to significant loss of fluid and electrolytes, causing dehydration and abdominal cramps. An enteric pathogen is an infectious agent capable of causing an enteric infection.

Prevention of enteric infection in a subject at risk of infection means neutralizing, inhibiting, blocking, or at least significantly reducing infection by an enteric pathogen, or preventing the symptoms of the associated disease of the intestine from manifesting themselves. Without wishing to be bound by theory, it is assumed that the colonization of the intestinal mucosa with the pathogen would be prevented or at least significantly reduced by the use of the composition of the invention, allowing the normal microflora of the intestine to become reestablished, and/or any toxins that the enteric pathogen produces would be neutralized or inhibited.

Prevention of recurrence of *Clostridium difficile* infection refers to the prevention of a new episode of diarrhea associated with a positive *C. difficile* test (e.g. *C. difficile* identification in stool) after discontinuation of antibiotic treatment of a previous *C. difficile* infection (regardless whether this antibiotic treatment is for a first or already a recurrent infection). Prevention of recurrence can be shown, for example, in a placebo-controlled trial, where the rate of recurrence is reduced by at least 40%, preferably at least 50%, more preferably at least 60%, even more preferably by at least 70%, 75% or even 80%, by the composition of the invention as compared with the placebo.

A subject at risk of infection is any person with an increased risk of becoming infected. For example, it may be a person travelling to a region where an enteric infection is endemic or is occurring more frequently than average, or a patient admitted to a hospital, person in a health care facility/nursing home, in particular an immunocompromised or an elderly patient. A subject at risk may also be a health care worker caring for patients potentially infected with highly contagious enteric pathogens that could lead to severe disease. Particularly in the case of *C. difficile* infections, a patient who has just recovered from a *C. difficile* infection through treatment with antibiotics is a subject at risk of infection. As mentioned above, the recurrence rate for *C. difficile* infection is high, and recurrence of the infection is difficult to treat due to the development of resistance of the bacteria to the antibiotics during the course of the primary treatment. In addition, a continued presence of resistant spores of *C. difficile* also contributes to the high recurrence rate.

The term sequelae in general refers to a pathological condition resulting from a disease, injury or trauma. In the current context, it refers to a pathological condition resulting from an enteric infection, in particular from recurrent *Clostridium difficile* infection. Sequelae from enteric infection may include, but are not limited to, chronic inflammation of the intestine or colitis, but also extragastrointestinal sequelae such as arthritis, joint inflammation, urinary tract infection, endometriosis, respiratory infections, and cardiac infections.

LIST OF FIGURES

The invention will now be illustrated by the following, non-limiting examples, with reference to the following figures and sequence listing:

FIG. 1 shows dot blots testing the binding of plasma-derived IgM and IgA to clinical isolates.

FIG. 4 shows the neutralization of *C. difficile* Toxin B by different immunoglobulin preparations.

Figure 1A:
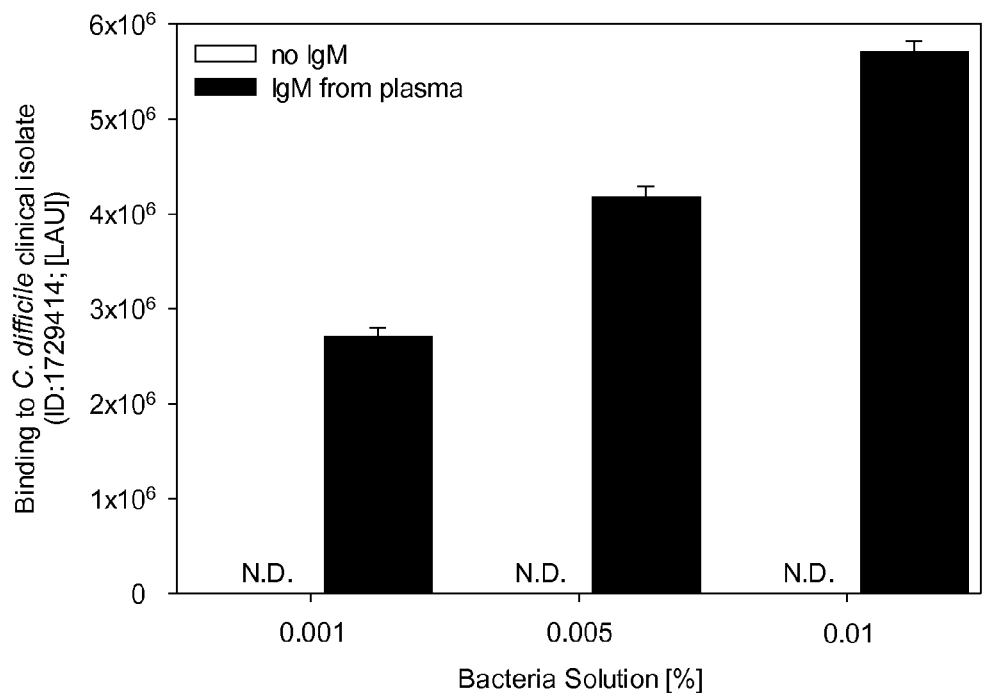
FIG. 1A shows the binding to clinical isolates of *C. difficile*.
Figure 1A:
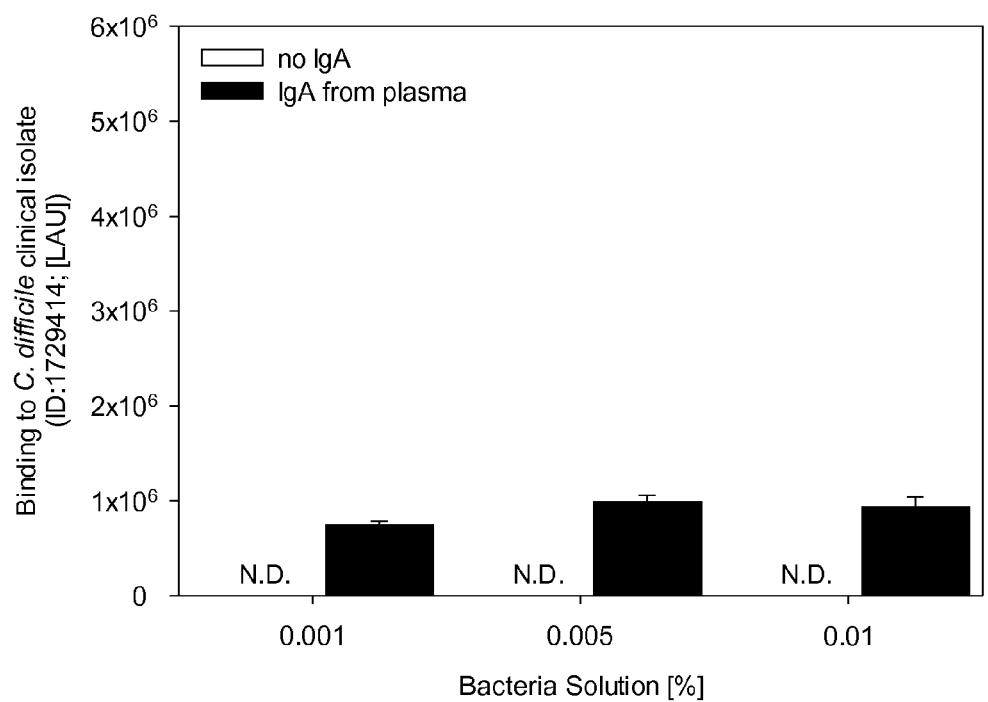

Sequence ID NO: 1 shows the sequence of the human pIgR (also available as SwissProt entry P01833)

EXAMPLES

The invention will now be exemplified by the following examples. These are intended to illustrate but not limit the invention.

Example 1: Binding of IgM and IgA to *C. difficile*, *S. enteritidis*, *S. flexneri*/Species and *E. faecium* Bacteria (Dot Blot)

Binding of plasma derived immunoglobulins to clinical isolates of different bacteria was tested by dot blot.

Materials and Methods 1.1 IgA Production by Affinity Chromatography from Plasma and by Sequential Elution of an Anion Exchange (MPHQ) Column Total human plasma IgA was purified from cryo-depleted pool plasma by affinity chromatography using CaptureSelect Human IgA resin (Bioaffinity Company BAC, Naarden, Netherlands) according to the resin manufacturer protocol. Briefly, cryo-depleted pool plasma, was diluted in phosphate buffered saline (PBS) to an IgA concentration of approximately 1 mg/mL and then loaded onto a PBS-equilibrated CaptureSelect Human IgA column, without exceeding the IgA binding capacity of the column. After loading the column was washed with PBS, and IgA was eluted with glycin buffer at pH 3. The eluate was adjusted with Tris to pH 4.5 and concentrated up to 16 mG/mL protein in PBS.

From the anion-exchange chromatography step of the IVIg manufacture process of CSL Behring AG (Berne, Switzerland), fraction F4 was obtained after a post-wash of the Macro-Prep High Q (Bio-Rad, Hercule, Calif.) column with 10 mM phosphate/30 mM acetate at pH 6.5 by elution with 55 mM tartrate/5 mM acetate at pH 7.6. Fraction F5 was subsequently eluted with 50 mM phosphate/25 mM citrate at pH 5.0. F4 and F5 were brought to approximately 1 mg/mL in PBS by ultra-/diafiltration, and then depleted of IgG by affinity chromatography using IgSelect resin (GE Healthcare, Glattbrugg, Switzerland). IgA F4 was directly harvested in the flowthrough of the IgSelect chromatography of F4 load. To obtain IgA F5, the IgSelect flowthrough of F5 load was depleted of IgM by affinity chromatography using CaptureSelect Human IgM resin (Bioaffinity Company BAC). IgA F4 and IgA F5 were brought to final concentrations by ultra-/diafiltration.

1.2 Dot Blot for *Clostridium difficile*

A patient sample of *Clostridium difficile* (ID 1729414, IFIK, University Hospital, Berne, Switzerland) stored at −80° C., in phosphate buffered saline, pH 7.4 (later referred to as PBS only; Dr. Bichsel AG, Interlaken, Switzerland) containing 30% glycerol (Sigma-Aldrich, Buchs/SG, Switzerland), was thawed and used for dot blot assays. Before dotting, the pellet was washed once in PBS (centrifugation at 5000 rpm during 10 min at RT). The bacteria pellet was then resuspended in 30 microL PBS, resulting in a 1% (w/v) bacteria solution. This solution was serially diluted to 0.01, 0.005 and 0.001% (all w/v). The different bacteria solutions were then dotted (1 microL per dot, duplicates) on nitrocellulose filters (Whatman, Sigma-Aldrich, Buchs/SG, Switzerland) and dried until the dots became invisible.

The dry nitrocellulose with the dotted bacteria was blocked in PBS, containing 5% milk powder (RapidMilk, Migros, Berne, Switzerland) during 30 min at RT and washed twice in PBS, containing 0.05% Tween20 (BioRad, Reinach/BL, Switzerland), and twice in PBS only (5 min per washing step, shaking, RT). The nitrocellulose was then cut into strips: Each strip having all 3 concentrations of the dotted bacteria (in duplicates) on it.

The single strips were then incubated (1 h at RT) with the previously diluted Ig preparation (IgG, IgAs and IgMs). The Igs were diluted in PBS, containing 5% milk powder, to a concentration of 100 microG/mL. Negative controls were bacteria-dotted strips which were incubated with PBS containing 5% milk powder only. After 1 h incubation at RT, the strips were washed three times (as described above) in PBS containing 0.05% Tween20, followed by two washes in PBS containing 0.1% $NaN_3$ and once in PBS only.

The strips, including the strips used as negative controls, were then incubated with the corresponding Ig isotype-specific horseradish-peroxidase- (HRP-) labeled antibodies (Dako, Baar, Switzerland). After three washing steps in PBS, containing 0.05% Tween20 and three washes in PBS only (all done as described above), the strips were developed applying the Enhanced Chemiluminescence (ECL) method. The strips were incubated for 2 min (RT, shaking) with 0.5 mL of peroxide/luminol (mixed 1/1 (v/v)) solution (SuperSignal West, Thermo Fisher, Reinach/BL, Switzerland) and exposed during 60 sec in a luminescence image analyzer (ImageQuant, LAS 4000, GE Healthcare, Lausanne, Switzerland). The luminescence signal of each dot was quantified using the Image Quant Software, and expressed in light arbitrary units (LAU). Mean values of the dotted duplicates were calculated and the corresponding negative controls were subtracted.

1.3 Dot Blot (*S. flexneri*/Species, *E. faecium, S. enteritidis*)

Patient samples of *S. flexneri*/species, *E. faecium, S. enteritidis* (individual clinical isolates; IFIK, University Hospital, Berne, Switzerland) stored at −80° C., in PBS, pH 7.4 (Dr. Bichsel AG, Interlaken, Switzerland) containing 30% glycerol (Sigma-Aldrich, Buchs/SG, Switzerland), were thawed and used for dot blot assays. Before dotting, the pellet was washed once in TBS (centrifugation at 5000 rpm during 10 min at RT). The bacteria pellet was then resuspended in 50 or 100 microL TBS respectively, and diluted to a 5% (w/v) bacteria solution in TBS. The different bacteria solutions were then dotted (1 microL per dot, duplicates) on nitrocellulose filters (Whatman, Sigma-Aldrich, Buchs/SG, Switzerland) and dried until the dots became invisible.

The dry nitrocellulose with the dotted bacteria was blocked in TBS, containing 5% milk powder (RapidMilk, Migros, Berne, Switzerland) during 30 min at RT and washed twice in TBS, containing 0.05% Tween20 (BioRad, Reinach/BL, Switzerland), and twice in TBS only (10 min per washing step, shaking, RT). The nitrocellulose was then cut into strips: Each strip having 4 different bacteria isolates (in duplicates) on it.

The single strips were then incubated (1 h at RT) with the previously diluted Ig preparation (IgG, IgAs and IgMs). The Igs were diluted in TBS, containing 5% milk powder, to a concentration of 1 mg/mL. Negative controls were bacteria-dotted strips which were incubated with TBS containing 5% milk powder only. After 1 h incubation at RT, the strips were washed three times (as described above) in TBS containing 0.05% Tween20, followed by three washes in TBS only.

The strips, including the strips we used as negative controls, were then incubated with the corresponding Ig isotype-specific alkaline phosphatase (AlcPhos)-labeled F(ab')$_2$-fragments (Jackson Immuno Research, Suffolk, United Kingdom) during 30 min at RT (shaking). After three washing steps in TBS, containing 0.05% Tween20 and three washes in TBS only (all done as described above), the strips were developed applying the AlcPhos-Developing Kit (Bio-Rad, Reinach/BL, Switzerland). The strips were incubated for 2 min (RT, shaking) with 1 mL of previously prepared (according to package insert) developing solution followed by two washes in $H_2O_{ad\ inject}$ (B. Braun Medical AG, Sempach, Switzerland; 1-2 min per washing step, RT, shaking). Pictures of the developed strips were then taken using an image analyzer (ImageQuant, LAS 4000, GE Healthcare, Lausanne, Switzerland). The resulting dots were then quantified using the Image Quant Software, and expressed in light arbitrary units (LAU). Mean values of the dotted duplicates were calculated and the corresponding negative controls were subtracted.

Each isolate was tested in two different experiments and mean values of the two results were calculated.

Results

The dot blots testing the binding of plasma-derived IgM and IgA to clinical isolates of *C. difficile* are shown in FIG. 1A. *C. difficile* bacteria were recognized by both IgM and IgA. The binding of IgM appeared to be stronger; however, due to the use of different detecting antibodies a direct comparison of the binding strength cannot be made.

Figure 1B:
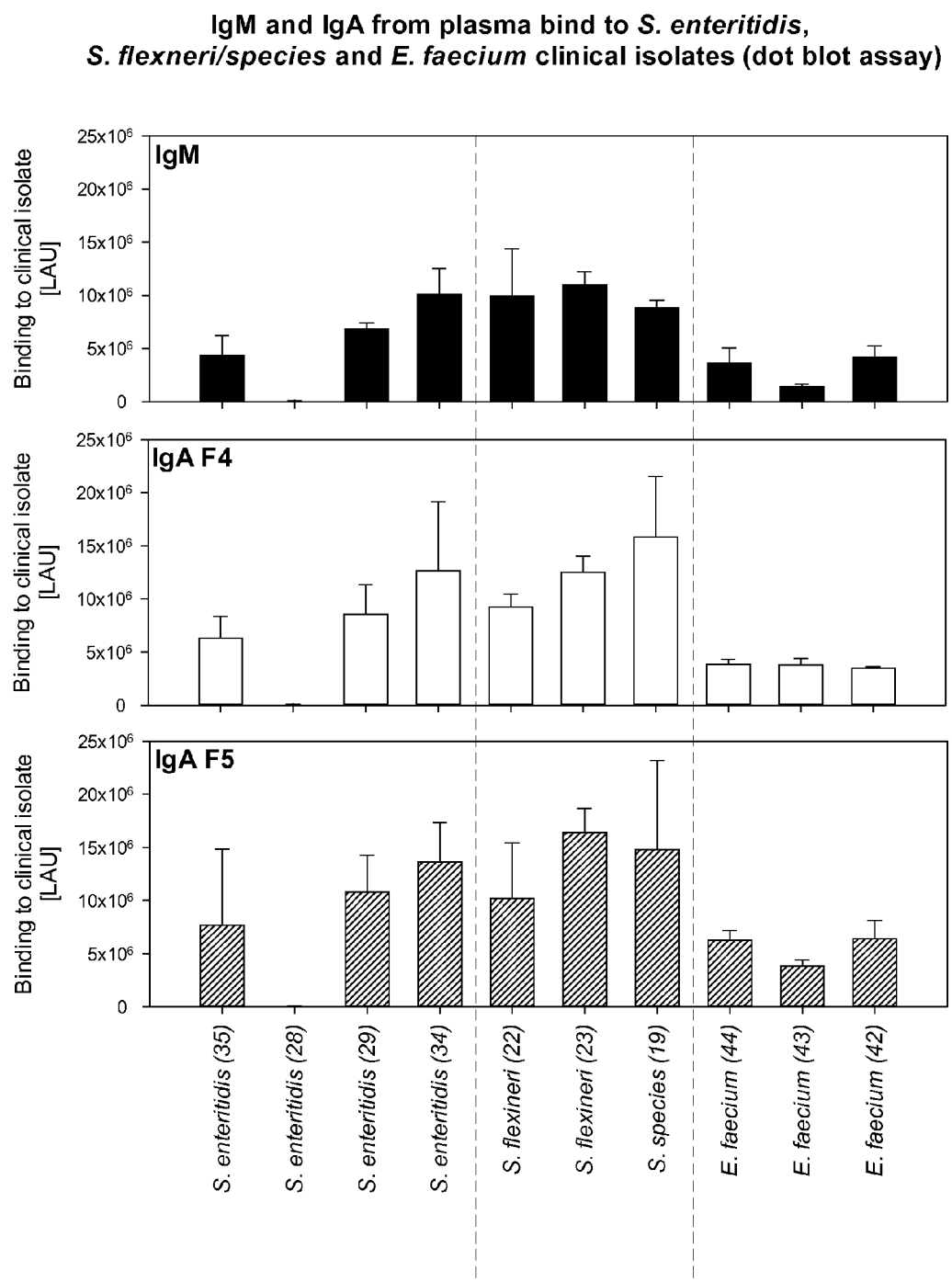
FIG. 1B shows the binding to clinical isolates of *S. enteritidis*, *S. flexneri*/species and *E. faecium*.

The dot blots on clinical isolates of *S. enteritidis*, *S. flexneri*/species and *E. faecium* are shown in FIG. 1B. *S. enteritidis*, *S. flexneri*/species and *E. faecium* bacteria were recognized by both IgM and IgA. The binding of IgA generally appeared to be stronger; however, due to the use of different detecting F(ab')$_2$-fragments a direct comparison of the binding strength cannot be made.

Example 2: Binding of Immunoglobulins to *C. difficile* Bacteria by Flow Cytometry To confirm the specificity of antibody binding to surface molecules of *C. difficile* bacteria the results obtained by dot blot were confirmed by flow cytometry.

A patient sample of *Clostridium difficile* (ID 1729414) stored in liquid nitrogen in PBS containing 30% glycerol was thawed and grown under anaerobic conditions overnight at 37° C. in thioglycollate bouillon. Bacteria were washed twice with PBS by centrifugation at 2000 g during 10 min at room temperature. The concentration was adjusted to $2 \times 10^6$ bacteria/mL by measuring the absorption of the suspension at 650 nm using the same buffer and using the relationship that extinction of 1.1 at 650 nm corresponds to $1 \times 10^9$ CFU/mL.

To assess the amount of immunoglobulin binding to the bacteria 250 microL of the bacteria suspension was pipetted into polypropylene tubes followed by 250 microL of the immunoglobulin product to be assessed. Immunoglobulin samples containing different protein concentration were assessed over an optimal concentration range. Samples primarily containing IgA, IgG or IgM, prepared as described in paragraph 1.1, were assessed. The samples containing the bacteria-immunoglobulin mixtures were incubated at room temperature for 1 hour before adding 2 mL of Hanks balanced salt solution containing 1 mg/mL bovine serum albumin (Hanks-BSA) at 2000 g for 10 min preferably at 4° C. Supernatants were discarded.

To prepare samples for FACS measurement, 100 microL of biotinylated anti-human immunoglobulin antibody solution at saturating concentrations were added to the tubes containing the immunoglobulin treated bacteria. As controls biotinylated mouse IgG of the same subclass as the anti-immunoglobulin antibodies used were also assessed at the same concentration. Samples were incubated for 30 min at 4° C. before adding 2 mL HBSA-BSA and centrifugation at 2000 g for 10 min at 4° C. The supernatants were discarded and 100 microL of saturating amounts of phycoerythrine labeled streptavidine, was added to the tubes before incubation for 30 min at 4° C. After centrifugation at 2000 g for 10 min at 4° C. and removal of supernatants, bacteria were fixed by adding 200 microL fixation solution such as Cellfix before measurement on the FACS.

At least 5000 bacteria/sample were measured on a FACS Canto II. Bacteria were identified by forward and 90° side scatter and fluorescence at the respective wave lengths within the bacterial population was assessed. Specific binding of the respective immunoglobulin class to the bacteria was calculated as the difference in fluorescence between samples incubated with the respective anti-immunoglobulin antibody and the mouse control antibody.

Figure 2:
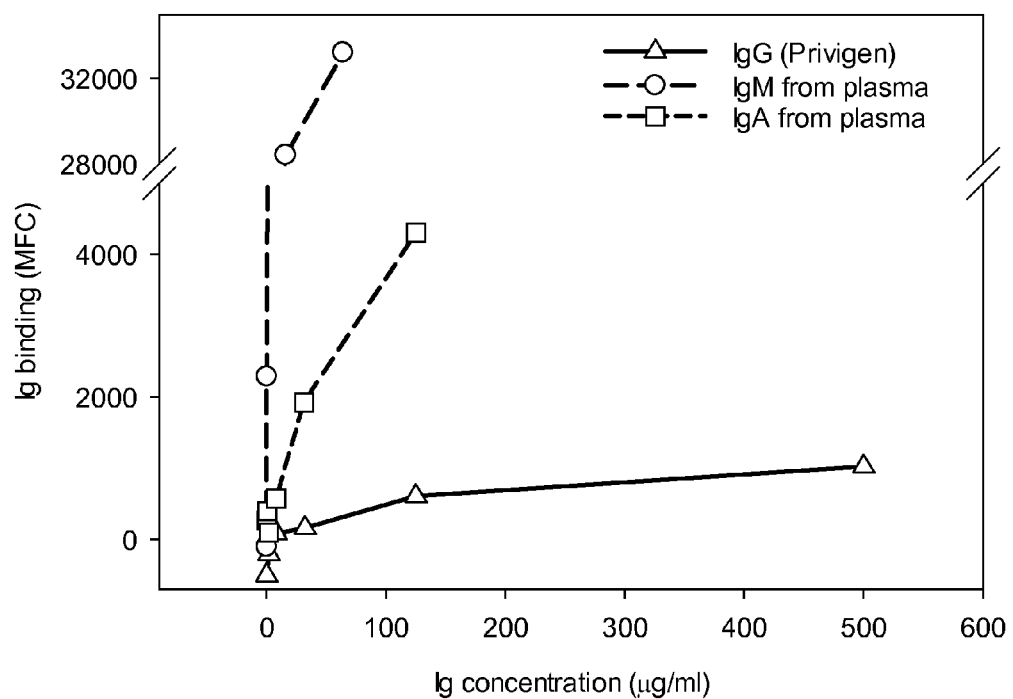
FIG. 2 shows the binding of different immunoglobulin preparations to clinical isolates of *C. difficile* by flow cytometry.

The results are shown in FIG. 2. It shows the dose-dependent binding of plasma-derived IgM, IgA and IgG to *C. difficile* bacteria. Again, strongest signals were obtained with IgM, whereas IgA showed weaker but clearly detectable binding. IgG only showed a weak binding to *C. difficile* bacteria in this test.

Example 3: Binding of IgA Preparations to Toxin A and B of *C. difficile* by ELISA Binding of various preparations of plasma-derived IgA to Toxins A and B of *C. difficile* was tested by ELISA.

Microplates (Nunc PolySorp, Fisher Scientific, Pittsburgh, Pa.) were coated overnight at 4° C. with 0.5 microG/mL toxin A, 2 microG/mL toxin B in carbonate-bicarbonate buffer (pH 9.6) (50 microL per well). After washing with PBS supplemented with 0.05% tween 20 (PBST) (200 microL per well), plates were saturated with 1% BSA/PBST (200 microL per well) for 1 hour followed by washing. Test samples, diluted in 0.1% BSA/PBST (100 microL per well), were incubated for 1 hour and tested in triplicate. Bound antibodies were detected using horseradish peroxidase-conjugated anti-immunoglobulin A (Dako Corporation, Carpinteria, Calif.) diluted 1:1000 in PBST/0.1% BSA (100 microL per well, 1 hour). After washing with PBST ×3 the substrate 3,3',5,5'-tetramethylbenzidine (Sigma) was added (50 microL). The reaction was stopped by addition of 1M phosphoric acid (50 microL) and optical density (O.D.) was measured at 450 nm (reference 630 nm).

Figure 3:
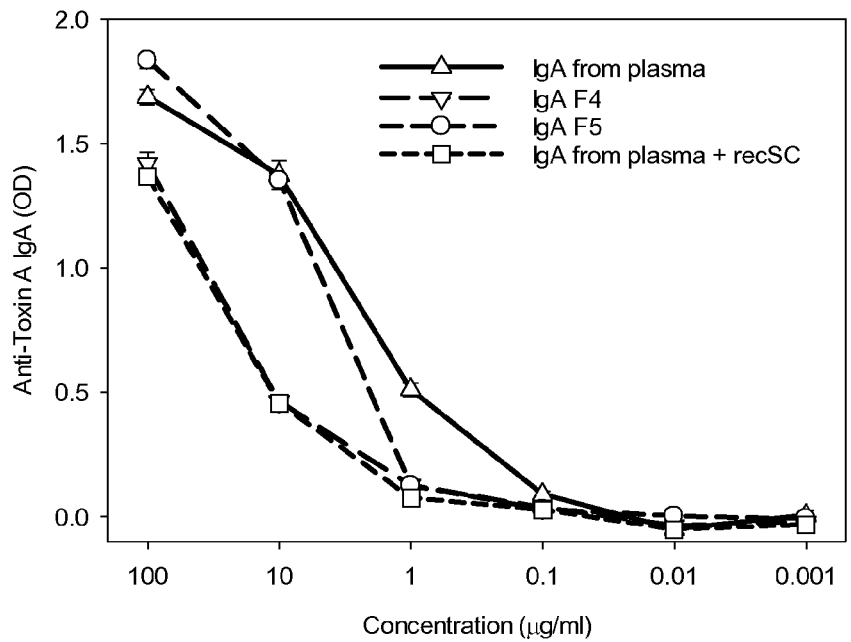
FIG. 3 shows the binding of different immunoglobulin preparations to *C. difficile* toxins.
Figure 3:
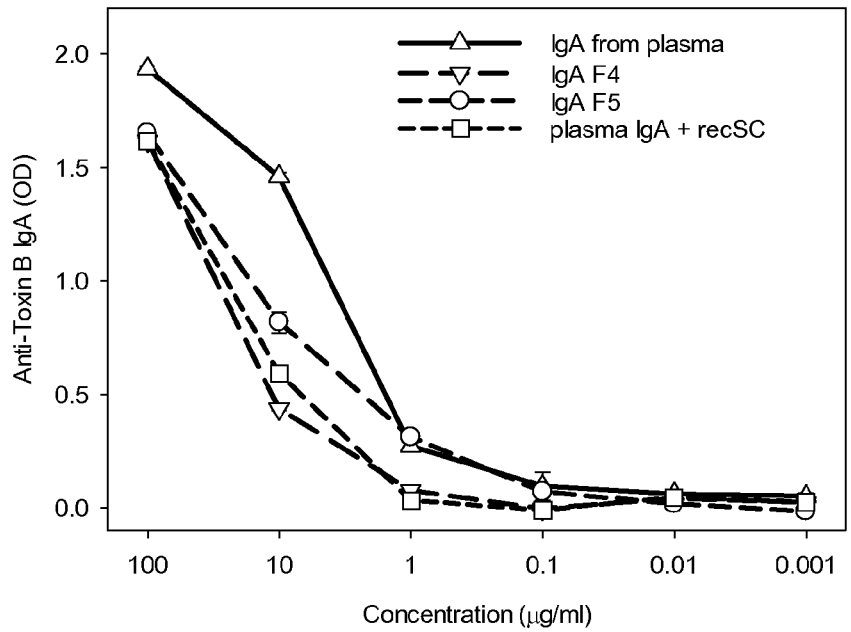

The results are shown in FIG. 3. FIG. 3A shows that IgA purified by affinity-chromatography directly from plasma as well as preparations IgA F4 and F5 derived from a side-fraction of the industrial IgG production process (see details in paragraph 1.1) bound effectively to Toxin A. Binding was comparable if IgA F5 was further associated with recombinant Secretory Component. As shown in FIG. 3B, similar results were obtained for binding to Toxin B of *C. difficile*.

Example 4: Neutralization of Toxic Effects of Toxin B of *C. difficile* with Immunoglobulins (Toxin Neutralization Assay)

To address in vitro whether binding to Toxin B of *C. difficile* had a functional consequence a toxin neutralization assay was used. In this test fibroblasts are exposed to Toxin B of *C. difficile* which leads to cell death if untreated.

The MRC-5 adherent fibroblast cell line (ATCC) was cultivated in Minimum Essential Medium supplemented with FCS (10% end concentration), L-alanyl-L-glutamine, gentamycine, sodium pyruvate and non-essential amino acids (medium) at 37° C. at 5% CO$_2$. Confluent cells were treated with 0.25% trypsin/EDTA (Gibco). After detachment cells were collected and washed by centrifugation for 10 min at 300 g at room temperature. Cells were taken up in medium, counted in a Neubauer chamber and cell concentration was adjusted to $4.0 \times 10^4$ cells/mL. The wells of a 96 flat bottom polystyrene microtiter plate were supplemented with 0.2 mL of the cells suspension and cells were allowed to adhere by overnight incubation at 37° C.

Optimum amounts of *Clostridium difficile* toxin B known to affect cells from preliminary experiments were mixed with increasing amount of the immunoglobulin sample, prepared as described in paragraph 1.1, to be tested and incubated at 37° C. for 30 min. Fifty microL of these mixtures were then added to the well of the microtiterplate containing the adhered cells. Incubation was continued for 24 hours in the incubator. Thereafter wells were observed in an inverted microscope for rounding. The extent of rounding was assessed by a visual score from −(cells healthy) and +(50% of cells rounded) to ++(all cells rounded/detached).

Figure 5:
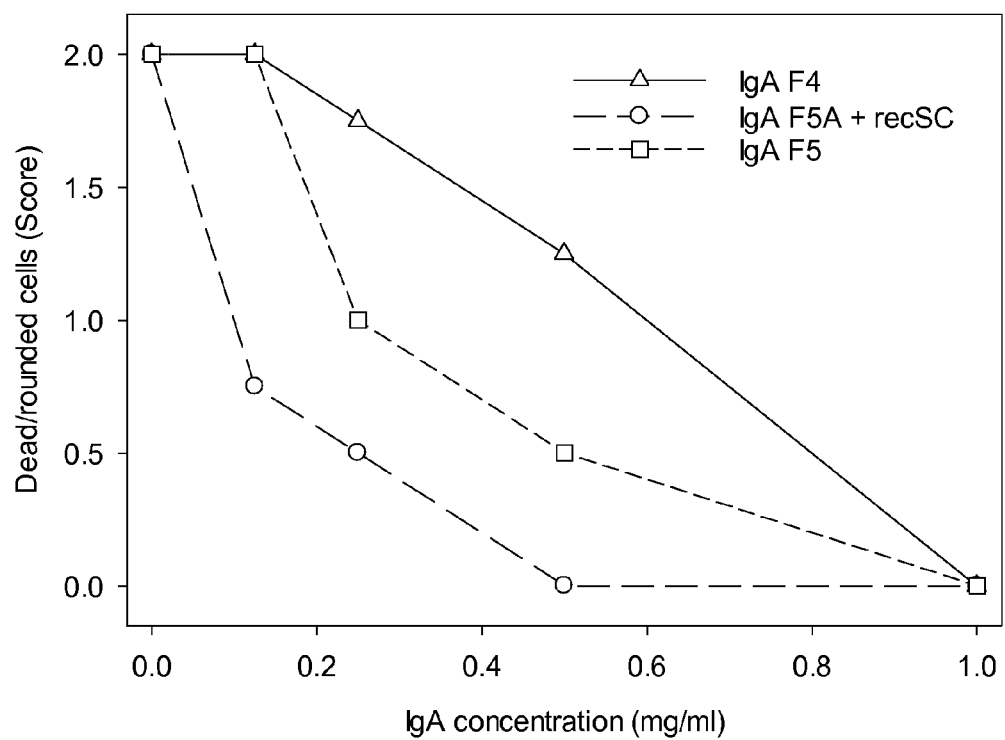
FIG. 5 shows the neutralization of *C. difficile* Toxin B by different IgA preparations.

The results are shown in FIGS. 4 and 5. FIG. 4 shows that plasma-derived IgA and IgG effectively protected fibroblasts from Toxin B-induced cell death, indicating neutralization of the toxin. In contrast, IgM was ineffective in toxin neutralization. Similarly, FIG. 5 shows that IgA preparations F4 and F5 both neutralized Toxin B, with apparently slightly better efficacy of IgA F5. As observed before in Example 3, IgA F5 associated with recombinant Secretory Component was also capable of binding to Toxin B. Here we show that it is also active in neutralizing the toxic effects of Toxin B.

Example 5: Primary Prevention of *C. difficile* Infection with IgA (Mouse Model)

To address the protective effect of IgA in vivo a mouse model of *C. difficile* infection was used.

C57BL/6 mice were housed in cages with free access to chow (Purina 5000) and tap water. Animals were treated with a mixture of oral antibiotics (kanamycin, gentamicin, colistin, metronidazole, and vancomycin) for 3 days as previously described (Chen et al (2008) Gastroenterology 135: 1984-92). Two days later, they were given parenteral clindamycin phosphate (10 mG/kg s.c.) [Day −1]. One day later [Day 0] they were challenged by gavage with $0.5 \times 10^5$ cfu of toxinogenic *C. difficile* strain 10465. A moderate to fulminant colitis developed 1 to 5 days after the administration of *C. difficile*. Untreated, this progresses rapidly into severe and fatal colitis in the majority of animals. The test compounds (suspended in carbonate buffer) were administered to groups at the dosage levels as shown in Table 1 (n=10 per group except group 4). Dosing (by gavage) started 1 day before *C. difficile* challenge [Day −1] and continued daily for 5 days.

TABLE 1

Experimental groups and dosing schedule

| Group No. | n= | Treatment[a] | Dose | Route of administration | Days of dosing[b] |
|---|---|---|---|---|---|
| 1 | 10 | Vehicle treated | NA | po (gavage) | −1 to 3 (5 doses) |
| 2 | 10 | Vancomycin | 50 mG/kg[c] | po (gavage) | −1 to 3 (5 doses) |
| 3 | 10 | IgA | 400 mG/kg | po (gavage) | −1 to 3 (5 doses) |
| 4 | 8 | IgA × Secretory Component | 400 mG/kg | po (gavage) | −1 to 3 (5 doses) |
| 5 | 10 | Vancomycin, followed by IgA | 50/400 mG/kg | po (gavage) | Vancomycin −1 to 3 (5 doses), followed by IgA 4 to 8 |
| 6 | 8 | Vancomycin, followed by IgA × Secretory Component | 50/400 mG/kg | po (gavage) | Vancomycin −1 to 3 (5 doses), followed by IgA 4 to 8 |
| 7 | 10 | Control | None | None | None |

[a]On Day −1 all except control animals receive clindamycin phosphate (10 mG/kg s.c.)
[b]On Day 0 all except control animals receive gavage with $0.5 \times 10^5$ cfu of C. difficile Animals were weighed daily and observed three times daily for morbidity and presence or absence of severe CDI with diarrhea. Animals judged to be in a moribund state [extended period of weight loss progressing to an emaciated state, anorexia for 24-48 hrs, prolonged lethargy (more than 3 days), signs of paralysis, skin erosions or trauma, hunched posture, distended abdomen] were euthanized by a single injection of sodium pentobarbital.

Mice are pre-treated with antibiotics before infection with *C. difficile*. For primary prevention of infection IgA (IgA F5) or IgA associated with recombinant Secretory Component (IgA F5+recSC) was given to mice via the oral route, starting 1 day before *C. difficile* infection for a total of 5 days (see details above; the preparation of the immunoglobulin fractions is described in paragraph 1.1). For control, vancomycin was given during the same period to another group of mice.

Figure 6:
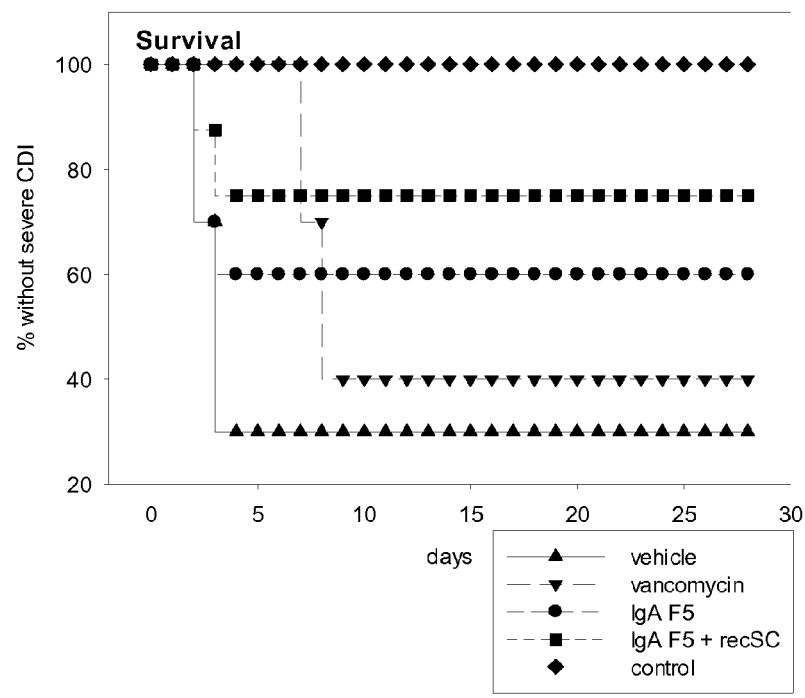
FIG. 6 shows the prevention of *C. difficile* infection by IgA and IgA with recombinant secretory component.
Figure 6:
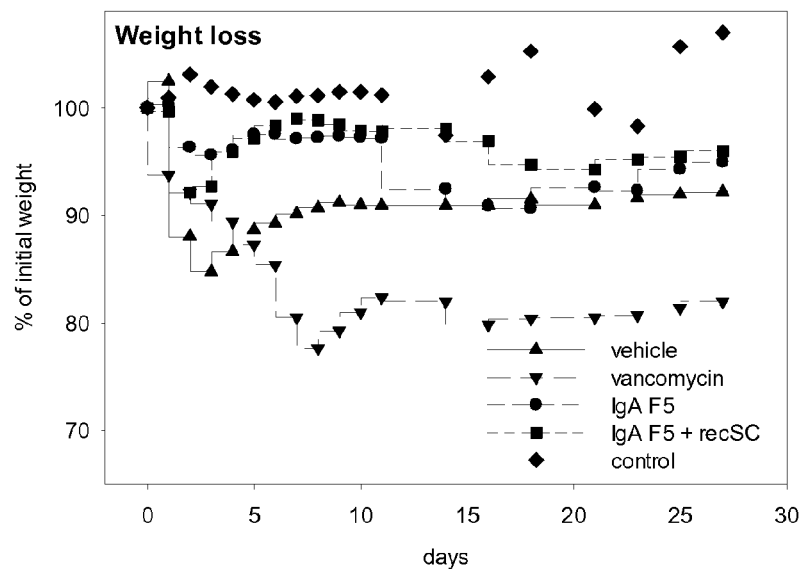

The results are shown in FIG. 6. The survival rate of infected, untreated mice was only 30%. Vancomycin effectively prevented death induced by *C. difficile* infection, however after stopping vancomycin treatment at day 4 a large fraction of animals (60%) suffered from recurrence of *C. difficile* infection, indicating that by vancomycin infection had not been totally cleared. Ultimately the survival rate in the vancomycin-treated group was only 40%. Treatment with plasma-derived IgA F5 led to a survival rate of 60% of mice and treatment with IgA F5+recSC even to a survival rate of 75%. None of the surviving IgA-treated animals developed recurrence. Thus, treatment with IgA preparations for primary prevention was not as effective as treatment with vancomycin but the effect was much more sustainable, i.e. no recurrence of infection was observed in mice that had survived primary infection. The degree of weight loss in surviving animals documents as well that severity of infection was dampened with IgA F5 or IgA F5+recSC.

Example 6: Prevention of Recurrence of *C. difficile* Infection with IgA (Mouse Model)

We addressed whether IgA preparations might prevent the high rate of recurrence of *C. difficile* infection observed after standard treatment with vancomycin. The experiments were essentially carried out as described in Example 5. To study recurrence of CDI animals surviving primary *C. difficile* challenge were maintained under observation until day 28. Animals were weighed 3 times weekly from day 7 to 28. Mice with recurrent CDI (according to the features described above) and judged to be in a moribund state were euthanized by a single injection of sodium pentobarbital.

Figure 7:
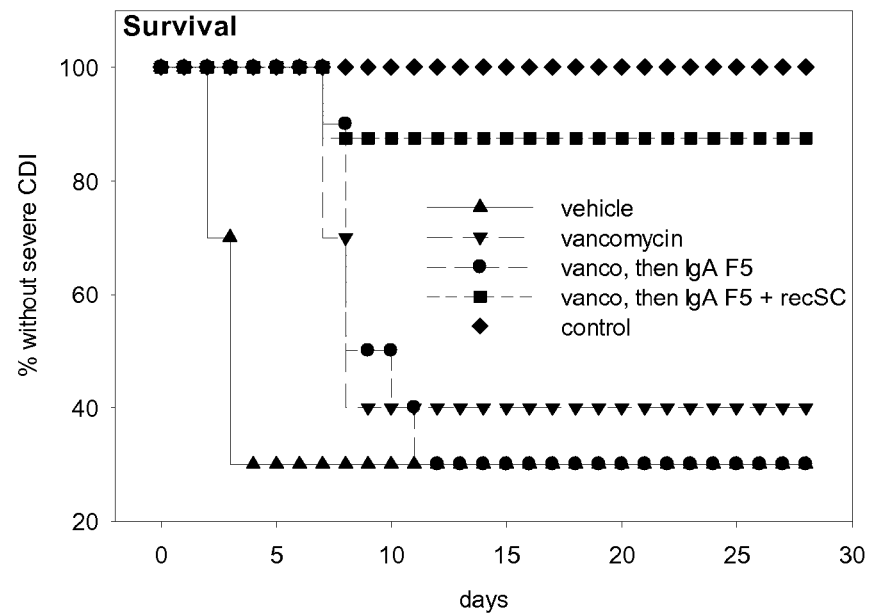
FIG. 7 shows the prevention of recurrence of *C. difficile* infection by IgA and IgA associated with recombinant secretory component after treatment of the primary infection with vancomycin.
Figure 7:
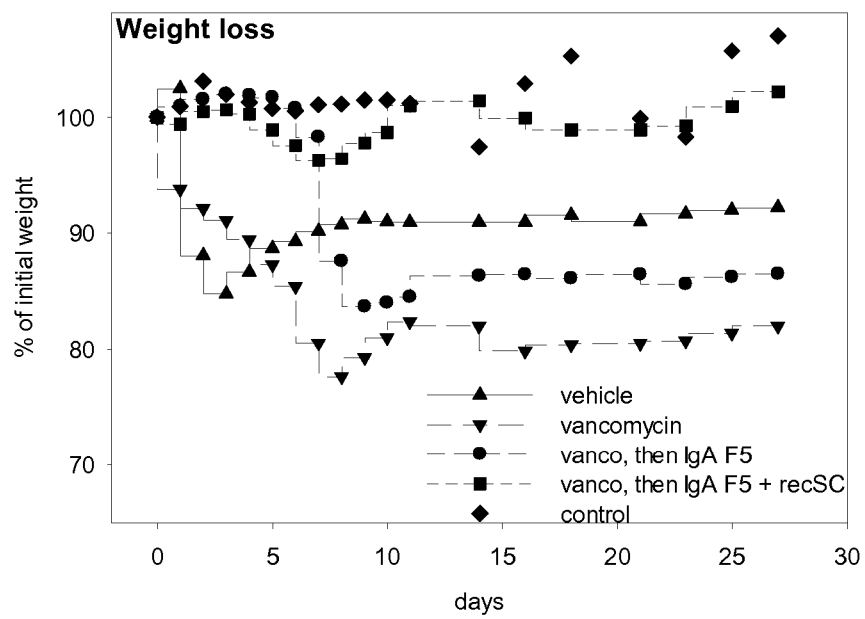

Mice infected with *C. difficile* and receiving primary treatment with vancomycin (day −1 to 3, 5 doses) as described above (Example 5) were given IgA F5 or IgA F5+recSC immediately after the last treatment of vancomycin (day 4 to 8, 5 doses). FIG. 7 shows that treatment with vancomycin only leads to a high rate of recurrence of infection (6 out of 10 animals; same data as above). Treatment with IgA F5 did not influence the recurrence rate. In contrast, treatment with IgA F5+recSC led to a dramatically reduced rate of recurrence (1 out of 8 animals). Again, the effect of treatment with IgA F5+recSC was also reflected in low weight loss in surviving animals compared to the vancomycin group.

Example 7: Prevention of Recurrence of *C. difficile* Infection with Monoclonal IgA Specific for *C. difficile* Toxin (Mouse Model)

In the same animal model as described in Examples 5 and 6 mice receiving vancomycin for primary treatment of *C. difficile* infection are treated with monoclonal IgA antibodies specific for *C. difficile* Toxin A or Toxin B or a mix of antibodies for these 2 antigens. The monoclonal IgA is used as monomers or dimers and can be or not associated with recombinant secretory component. The monoclonal IgA is used at the same dose as plasma-derived IgA or preferably at a much lower dose. This treatment is very effective at preventing recurrence of *C. difficile* infection ensuing after stopping primary treatment with vancomycin, especially in the group that was treated with dimeric IgA associated with recombinant secretory component.

Example 8: Prevention of *Salmonella* Infection with Polyclonal IgA/IgM (Animal Model)

Mice are treated orally with plasma-derived immunoglobulin, comprising IgA and IgM as the main components. The IgA/IgM-mix is further associated with recombinant secretory component or not. The compositions are used at concentrations similar to those described in examples 5 and 6. Thereafter mice are infected with *Salmonella*, e.g. *S. typhi* or *S. typhimurium*. The treatment with IgA/IgM associated with recombinant secretory component is very effective at preventing *Salmonella* infection.

Example 9: Prevention of *Enterococcus* Infection with Polyclonal IgA/IgM (Animal Model)

Mice are treated orally with plasma-derived immunoglobulin, comprising IgA and IgM as the main components. The IgA/IgM-mix is further associated with recombinant secretory component or not. The compositions are used at concentrations similar to those described in examples 5 and 6. Thereafter mice are infected with *Enterococcus*, e.g. *E. faecalis* or *E. faecium*. The treatment with IgA/IgM associated with recombinant secretory component is very effective at preventing *Enterococcus* infection.

The invention claimed is:

1. A method of preventing or preventing recurrence of an infection by an enteric pathogen in a subject at risk of infection, which comprises:
administering to the subject an effective amount of a composition comprising a secretory component and an immunoglobulin, said immunoglobulin derived from pooled human plasma,
wherein the enteric pathogen is *C. difficile, S. enteritidis, S. flexneri,* and/or *E. faecium,* and wherein the immunoglobulin comprises J chain-containing IgA.

2. The method of claim 1, wherein the subject at risk of infection has received antibiotic treatment for a primary *Clostridium difficile* infection.

3. The method of claim 1, wherein the secretory component is a recombinant secretory component.

4. The method of claim 3, wherein the recombinant secretory component is produced in a mammalian cell line.

5. The method of claim 1, wherein the secretory component is isolated from a natural source.

6. The method of claim 1, wherein the secretory component is human.

7. The method of claim 1, wherein the secretory component is the extracellular portion of a polymeric immunoglobulin receptor pIgR.

8. The method of claim 1, wherein the J chain-containing IgA comprises dimeric IgA.

9. The method of claim 1, wherein the IgA comprises anti-*Clostridium* and/or antitoxin IgA.

10. The method of claim 1, wherein the immunoglobulin further comprises IgM.

11. The method of claim 1, wherein administration is accomplished by oral or anal administration.

12. The method of claim 1, wherein administration of the composition is initiated after successful treatment of a *Clostridium difficile* infection by one or more antibiotics.

13. The method of claim 12, wherein administration of the composition is initiated up to 48 hours prior to conclusion of antibiotic treatment, or when antibiotic treatment is concluded, or shortly after conclusion of antibiotic treatment.

14. The method of claim 1, wherein administration of the composition prevents or prevents recurrence of sequelae of the enteric infection.

15. The method of claim 1, wherein the enteric pathogen is *S. enteritidis.*

16. The method of claim 1, wherein the enteric pathogen is *S. flexneri.*

17. The method of claim 1, wherein the enteric pathogen is *E. faecium.*

18. A method of preventing or preventing recurrence of an infection by an enteric pathogen in a subject at risk of infection, which comprises:
administering to the subject an effective amount of a composition comprising a secretory component and an immunoglobulin, said immunoglobulin derived from pooled human plasma, wherein the enteric pathogen is *Clostridium difficile,* and wherein the immunoglobulin comprises J chain containing IgA.

19. The method of claim 1, wherein at least 30% of the immunoglobulin of the composition is J-chain containing IgA.

20. The method of claim 1, wherein the composition prevents recurrence of *C. difficile* for at least 1 month after administration.

21. The method of claim 13, wherein the antibiotic is vancomycin.

* * * * *

SEQUENCE LISTING

```
<160> NUMBER OF SEQ ID NOS: 1

<210> SEQ ID NO 1
<211> LENGTH: 764
<212> TYPE: PRT
<213> ORGANISM: Homo sapiens

<400> SEQUENCE: 1

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
```

```
            260                 265                 270
Gln Ser Ser Gly Glu Asn Cys Asp Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Ser Val Ala
        355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
    610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685
```

```
Ser Arg Glu Phe Gly Ala Asn Asp Asn Met Gly Ala Ser Ser Ile Thr
    690             695             700

Gln Glu Thr Ser Leu Gly Gly Lys Glu Glu Phe Val Ala Thr Thr Glu
705             710             715                 720

Ser Thr Thr Glu Thr Lys Glu Pro Lys Lys Ala Lys Arg Ser Ser Lys
            725             730                 735

Glu Glu Ala Glu Met Ala Tyr Lys Asp Phe Leu Leu Gln Ser Ser Thr
            740             745             750

Val Ala Ala Glu Ala Gln Asp Gly Pro Gln Glu Ala
    755             760
```